(12) United States Patent
Jarverud et al.

(10) Patent No.: US 9,436,801 B2
(45) Date of Patent: Sep. 6, 2016

(54) HEMODYNAMIC STATUS ASSESSMENT

(75) Inventors: Karin Jarverud, Solna (SE); Anders Bjorling, Solna (SE); Malin Hollmark, Solna (SE); Kjell Noren, Solna (SE); Tomas Svensson, Stockholm (SE); Stefan Hjelm, Balsta (SE)

(73) Assignee: St. Jude Medical AB, Jarfalla (SE)

( * ) Notice: Subject to any disclaimer, the term of this patent is extended or adjusted under 35 U.S.C. 154(b) by 329 days.

(21) Appl. No.: 14/000,844

(22) PCT Filed: Mar. 18, 2011

(86) PCT No.: PCT/EP2011/054164
§ 371 (c)(1),
(2), (4) Date: Aug. 21, 2013

(87) PCT Pub. No.: WO2012/126503
PCT Pub. Date: Sep. 27, 2012

(65) Prior Publication Data
US 2013/0325359 A1 Dec. 5, 2013

(51) Int. Cl.
G01N 33/48 (2006.01)
G01N 33/50 (2006.01)
G06F 19/00 (2011.01)
A61B 5/053 (2006.01)
A61N 1/365 (2006.01)
G06F 19/24 (2011.01)
G06F 19/12 (2011.01)
A61B 5/0464 (2006.01)

(52) U.S. Cl.
CPC ............ *G06F 19/34* (2013.01); *A61B 5/0538* (2013.01); *A61N 1/36521* (2013.01); *G06F 19/3437* (2013.01); *A61B 5/0464* (2013.01); *A61N 1/36535* (2013.01); *G06F 19/12* (2013.01); *G06F 19/24* (2013.01)

(58) Field of Classification Search
None
See application file for complete search history.

(56) References Cited

U.S. PATENT DOCUMENTS

| 4,562,843 A | 1/1986 | Djordjevich et al. |
| 6,413,223 B1 | 7/2002 | Yang et al. |
| 2007/0142866 A1 | 6/2007 | Li et al. |
| 2010/0030086 A1 | 2/2010 | Zielinski et al. |

FOREIGN PATENT DOCUMENTS

| WO | WO 2010/024738 A1 * | 3/2010 |
| WO | WO 2011/134499 A1 * | 11/2011 |

OTHER PUBLICATIONS

International Search Report—Int'l App No. PCT/EP2011/054164; Int'l Filing Date: Mar. 18, 2010.
Written Opinion of the Int'l Searching Authority—Int'l App. No. PCTEP2011/054164; Int'l Filing Date: Mar. 18, 2011.

* cited by examiner

*Primary Examiner* — Russell S Negin

(57) ABSTRACT

A patient-specific hemodyanmic status model is determined from impedance data collected during periods of normal and abnormal hemodynamic status by deriving parameter values of a set of multiple impedance-derivable parameters from impedance signals collected during periods of normal hemodynamic status and in connection with periods of abnormal hemodynamic status. The parameter values are employed to estimate coefficients of a linear parametric status model. These coefficients can then be used together with parameter values determined from impedance signals determined during status assessment periods in order to determine a current hemdoynamic status of the patient.

7 Claims, 8 Drawing Sheets

HEMODYNAMIC STATUS ASSESSMENT

CROSS REFERENCE TO RELATED APPLICATION(S)

This is a U.S. national stage application of International Application No. PCT/EP2011/054164, filed Mar. 18, 2011.

TECHNICAL FIELD

The present invention generally relates to hemodynamic status assessment, and in particular to such status assessment based on a patient-specific parametric status model.

BACKGROUND

In cardiac patient care and treatment, there is a need to measure cardiac hemodynamic parameters such as blood volumes, blood flow, blood pressure etc. In order to adapt cardiac therapy, continuous information on hemodynamic status is generally necessary. This is true for both parameter optimization of implantable medical devices (IMDs), such as pacemakers, defibrillators and cardioverters, and drug therapy optimization. For patients having an IMD, these measurements often involve highly advanced sensors with complex design including specialized implantable medical leads with miniaturized electronics and sensors in the tip of the implantable medical lead. There is, though, a need for a simple solution to assess and predict the hemodynamic status of patients without the requirements of having specialized equipment and dedicated sensors implanted in the patient's body.

US 2009/0264716 discloses an IMD that classifies a detected tachyarrhythmia as being ventricular tachycardia (VT) or non-VT tachyarrhythmia based on a hemodynamic signal representative of mechanical function of the cardiovascular system. The classification is based on comparing morphological features of the sensed hemodynamic signal to a template and determining a measure of morphological variability.

U.S. Pat. No. 7,062,326 discloses an IMD that determines a ventricular impedance signal and derives a parameter from the impedance signal. This parameter correlates closely to the physical workload and at the same time provides hemodynamic feedback information.

US 2007/0142866 discloses an IMD that records hemodynamic signals, derives parameters from the hemodynamic signals during normal rate and stores the parameters as reference template. When a tachyarrhythmia episode is detected based on the heart rate, the hemodynamic signals are anew recorded, the parameters are extracted therefrom and compared to the reference template. The comparison is employed to determine whether and/or when to deliver anti-tachycardia pacing.

US 2010/0030086 discloses an IMD that monitors intracardiac impedance to determine a change in hemodynamic status of a patient by detecting changes in impedance parameters over heart cycles. The determined impedance parameters are compared to previously determined values and are employed to detect any change in hemodynamic status.

There is still a need for an efficient and patient-specific technique to enable assessment of hemodynamic status in a reliable way.

SUMMARY

It is a general objective to enable patient-specific assessment of hemodynamic status.

It is a particular objective to enable generation and usage of a patient-specific parametric status model.

These and other objectives are met by embodiments disclosed herein.

An aspect of the embodiments relates to a system for determining a hemodynamic status model for a patient or subject. The system comprises a lead connector that is electrically connectable to at least two electrodes of at least one electric lead. A signal generator generates and applies electric signals over two electrodes and a portion of the subject both during a period of normal hemodynamic status of the subject and in connection with abnormal hemodynamic status of the subject. The resulting electric signals are sensed by a signal sensing unit using two electrodes during the period of normal hemodynamic status and in connection with the period of abnormal hemodynamic status. An impedance processor determines a first impedance signal based on the electric signals applied and the resulting electric signals sensed during the period of normal hemodynamic status. The impedance processor also determines a second impedance signal based on the electric signals applied and the resulting electric signals sensed in connection with the period of abnormal hemodynamic status. The system comprises a parameter processor that calculates first parameter values of a set of N≥2 different impedance-derivable parameters based on the first impedance signal and calculates second parameter values of the N parameters based on the second impedance signal. A model processor estimates N+1 coefficients of a linear parametric status model based on the first parameter values and the second parameter values, $$\text{Index}^j = c_0 + \sum_{i=1}^{N} c_i f_i^j,$$

where $j=1, 2$, $c_0$, $c_i$ represent the N+1 coefficients, $f_i^1$ represent the first parameter values, $f_i^2$ represent the second parameter values, $\text{Index}^1$ has a predefined first value representative of normal hemodynamic status of the subject and $\text{Index}^2$ has a predefined second value representative of abnormal hemodynamic status of the subject. The estimated coefficients are stored in a memory as representations of the linear parametric status model.

Another aspect of the embodiments defines an implantable medical device comprising a lead connector electrically connectable to at least two electrodes of at least one implantable medical lead. The lead connector is connected to a signal generator configured to generate electric signals that are applicable over two of the connectable electrodes during a status assessment period. A signal sensing unit is configured to sense resulting electric signals over two connectable electrodes during the status assessment period. An impedance processor of the implantable medical device determines an impedance signal based on the applied electric signals and the sensed resulting electric signals. The impedance signal is processed by a parameter processor that is configured to calculate parameter values of a set of N≥2 different impedance-derivable parameters. The calculated parameters are employed by a status processor together with N+1 coefficients of a linear parametric status model, $$\text{Index} = c_0 + \sum_{i=1}^{N} c_i f_i,$$

wherein $c_0$, $c_i$ represent the N+1 coefficients and $f_i$ represent the parameter values calculated by the parameter processor, to calculate a hemodynamic status index for a subject. This hemodynamic status index is a specific index representative of the current hemodynamic status of the subject and is of high diagnostic value and can be used to select appropriate therapy, if needed, for the subject.

Further aspects of the embodiments relates to a method of determining the hemodynamic status model and to a method of assessing the hemodynamic status of a subject using such a hemodynamic status model.

The embodiments enable patient-specific assessment of the hemodynamic status of a patient. The patient-specificity achieved by the hemodynamic status model will generally improve the diagnosis of the patient and can thereby lead to more appropriate selection of therapy for the patient as compared to using population-general techniques according to the prior art.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The embodiments relate to systems and methods for assessing hemodynamic status of a patient or subject, preferably a mammalian subject and more preferably a human subject. According to the embodiments a patient-specific hemodynamic status model is determined and employed to assess the hemodynamic status of the subject. The patient-specific hemodynamic status model employed in the status assessment implies that a more reliable determination of the hemodynamic status of the subject is achieved as compared to using prior art techniques of comparing measured parameter values of, for instance, blood pressure and blood flow with defined threshold values. The reason behind this is that different subjects will respond quite differently in abnormal hemodynamic events. Thus, a given subject can, have a very low blood pressure and still not be severely ill, whereas another subject is unconscious and is in a life-threatening condition at the same blood pressure level. Thus, usage of general population-based threshold values and traditional hemodynamic parameters, such as blood pressure and blood flow, will run into problem with regard to hemodynamic status assessment due to the large population-wise difference in these parameter values among different subjects.

The embodiments, in clear contrast, determine and use a patient-specific hemodynamic status model that correctly reflects the characteristics of the given subject to thereby achieve a reliable prediction and assessment of the hemodynamic status of the given subject.

Figure 1:
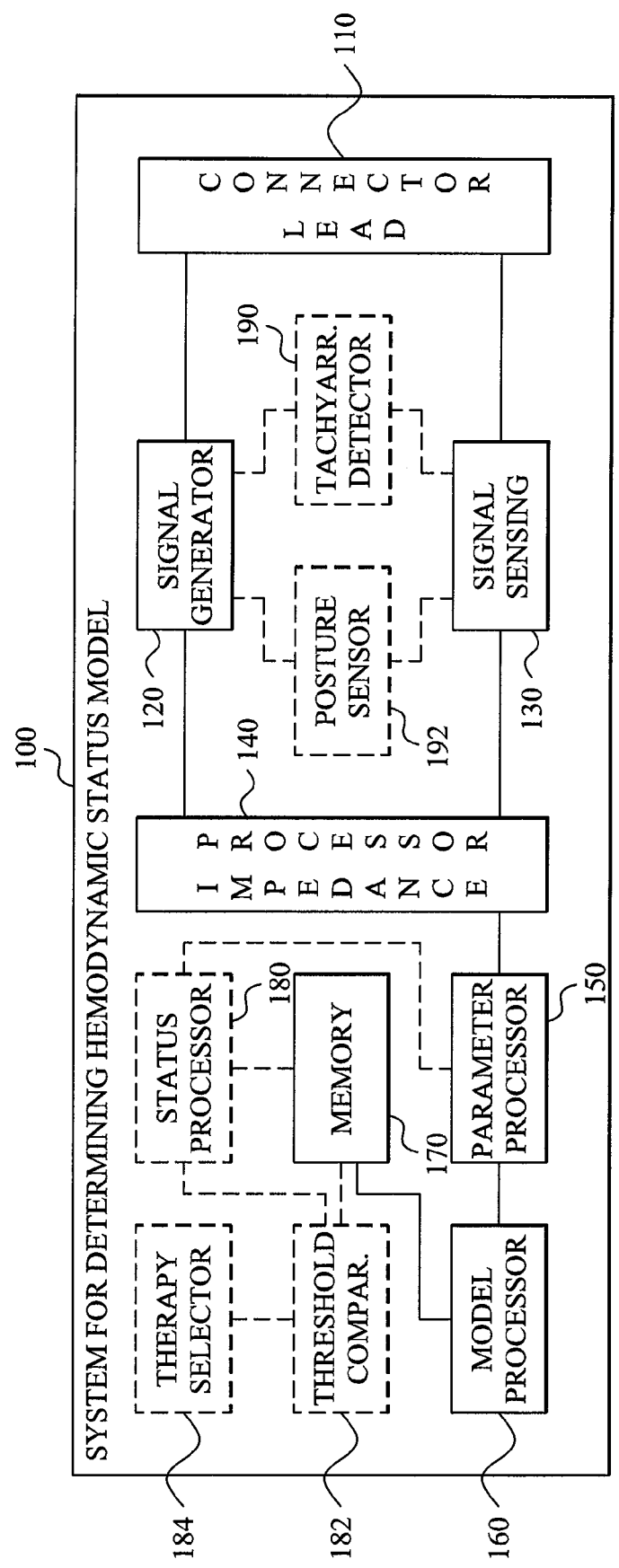
FIG. 1 is a schematic block diagram of a system for determining a hemodynamic status model according to an embodiment.

FIG. 1 is a schematic overview of a system 100 configured to determine a hemodynamic status model of a subject. The system 100 comprises an electrode, sensor or lead connector 110 that is electrically connectable to at least two electrodes. The at least two electrodes are provided on at least one electric lead connectable to the lead connector 110. Thus, the lead connector 110 can, in operation, be connected to a single electric lead comprising at least two electrodes, such as a bipolar lead with two electrodes, a tripolar lead with three electrodes or a quadropolar lead with four electrodes. Alternatively, the lead connector 110 is connectable to at least two leads, each having at least one electrode, such as unipolar leads (with one electrode), bipolar, tripolar or quadropolar leads.

Figure 2:
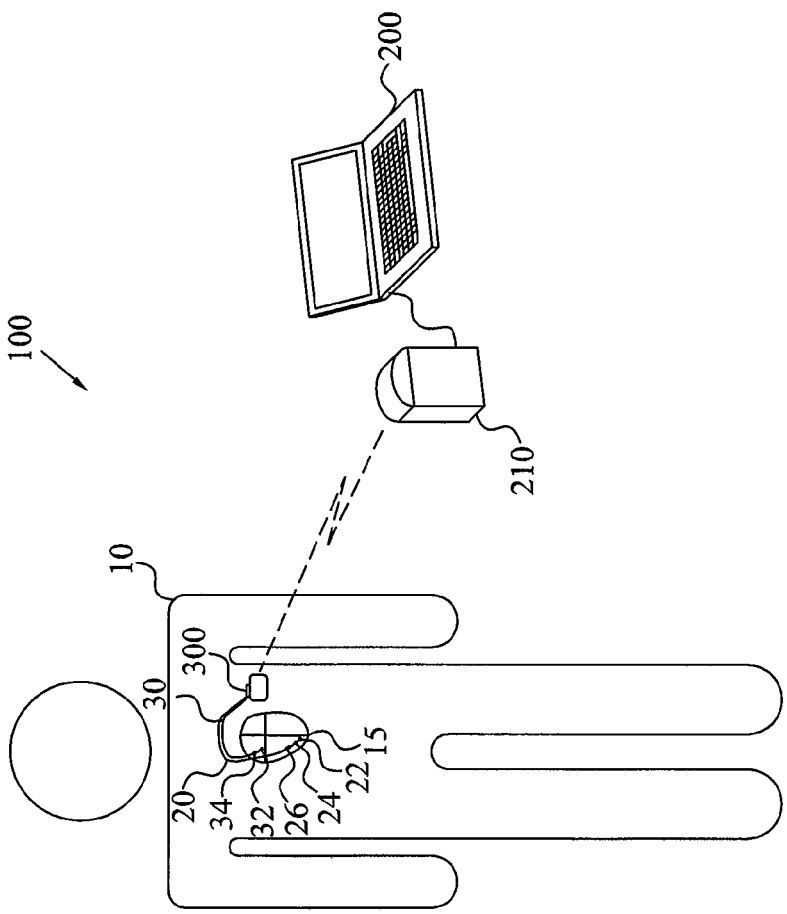
FIG. 2 is an illustration of a human subject and a system for determining a hemodynamic status model according to an embodiment.

The at least one lead could be an implantable medical lead. In such a case, the at least one implantable medical lead is preferably an intracardiac lead or an epicardial lead having electrodes positioned inside or in connection with the heart of a subject. FIG. 2 schematically illustrates a human subject 10 with two intracardiac leads 20, 30 exemplified as a right atrial lead 30 having electrodes 32, 34 provided in the right atrium of the subject's heart 15 and a right ventricular lead 20 having electrodes 22, 24, 26 provided in the right ventricle of the heart 15. Further variants of intracardiac leads that can be employed according to the invention include a left atrial lead and a left ventricular lead. The left ventricular lead is generally provided epicardially in the coronary system of the heart 15.

Figure 3:
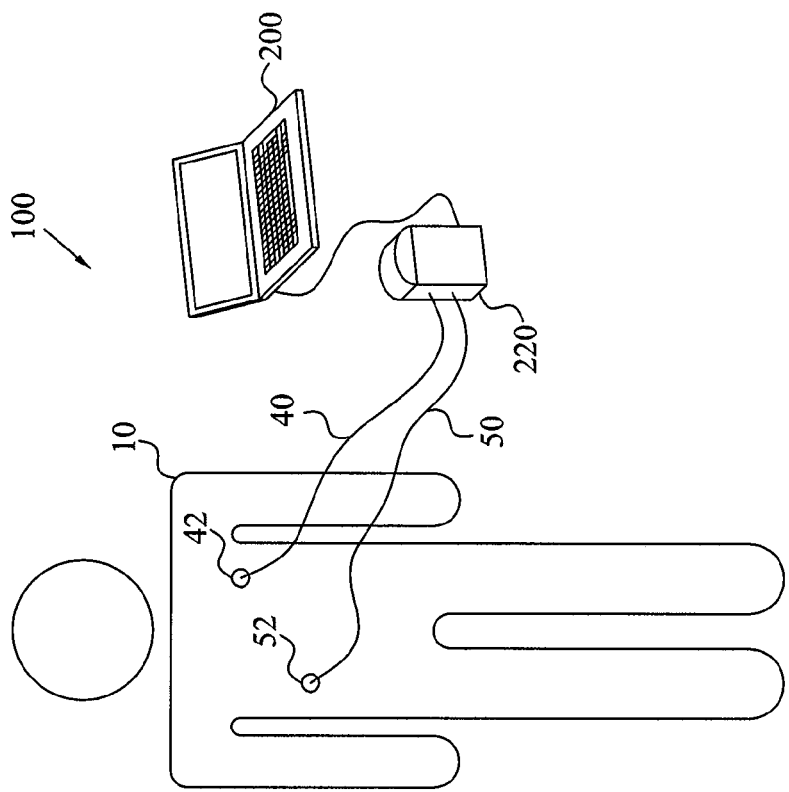
FIG. 3 is an illustration of a human subject and a system for determining a hemodynamic status model according to another embodiment.

In an alternative embodiment as illustrated in FIG. 3 the at least one lead 40, 50 is not implanted in the subject's body but rather has at least one electrode 42, 52 attached to the skin surface of the subject 10. In such a case, the electrodes 42, 52 are preferably attached to the skin surface of the thorax of the subject 10, such as illustrated in FIG. 3.

The system 100 as illustrated in FIG. 1 also comprises a signal generator 120 connected to the lead connector 110 and configured to generate electric signals that are applicable over two electrodes of the at least two electrodes connectable to the lead connector 110. In a particular embodiment, the signal applying electrodes are arranged to apply the electric signal in connection with the subject's heart.

The electric signals generated by the signal generator 120 are preferably AC signals having a defined time-dependent voltage/current profile. The electric signals are preferably sub-threshold electric signals implying that they do not trigger capture by the myocardium when applied to the heart.

According to the embodiments, the electric signals are generated by the signal generator 120 and applied using two electrodes connected to the lead connector 110 during a period of normal hemodynamic status of the subject and in connection with a period of abnormal hemodynamic status of the subject.

Thus, the embodiments generate and apply electric signals at different subject conditions where the subject is either at normal or healthy hemodynamic status and in connection with a period where the normal hemodynamic status deteriorates so severely that it becomes abnormal and combative actions are possibly required, such as defibrillation or acute medication, in order to stop the potentially life-threatening abnormal hemodynamic status and return back to normal hemodynamic status for the subject. At this period of abnormal hemodynamic status, the subject cannot maintain normal blood circulation and the blood circulation instead will be dangerously low, possibly causing the subject to faint if not increased back towards normal flow levels.

In a particular embodiment, the signal generator 120 generates and applies the electric signals during multiple different periods of normal hemodynamic status and in connection with multiple different periods of abnormal hemodynamic status. In such a case, more measurement data will be available for the system 100 when determining the hemodynamic status model. Hence, a more reliable hemodynamic status model can then be determined as compared to merely get measurement data in connection with a few periods or time instances.

There are numerous medical conditions that can cause an abnormal hemodynamic status in the subject. A typical example is various arrhythmias and in particular tachyarrhythmia. Other clinically relevant conditions that can cause an abnormal hemodynamic status according to the embodiments include vasovagal syncope and transient ischemic attacks. In vasovagal syncope, the blood pressure is reduced leading to syncope. Normally, prior to losing consciousness, the subject becomes bradycardic, i.e. the heart rate is too low. However, the blood pressure is reduced already in the so-called pre-syncopal phase where there is no drop in heart rate. In the syncopal phase, blood pressure drops are becoming more dominant, ultimately leading to a major drop in heart rate and blood pressure.

According to the embodiments, the above presented examples of clinically relevant conditions can be used to collect abnormal hemodynamics during a training period for determining a hemodynamic status model.

The system 100 also comprises a signal sensing unit 130 connected to the lead connector 110 and configured to sense resulting electric signals captured over the electrodes connectable to the lead connector 110. The resulting electric signals are preferably resulting AC signals originating from at least a portion of the heart. The sensed AC signals are further due to the applied AC signals generated by the signal generator 120. In similarity to the signal generator 120 that is operated during the period(s) of normal hemodynamic status and in connection with the period(s) of abnormal hemodynamic status, the signal sensing unit 130 conducts the signal sensing during the period(s) of normal hemodynamic status and in connection with the period(s) of abnormal hemodynamic status.

An impedance processor 140 is implemented in the system 100 and configured to determine a first impedance signal based on the electric signals generated by the signal generator 120 and applied during the period of normal hemodynamic status and the resulting electric signals sensed by the signal sensing unit 130 during the period of normal hemodynamic status. The impedance processor 140 correspondingly determines a second impedance signal based on the electric signals applied and the resulting electric signals sensed in connection with the period of abnormal hemodynamic status of the subject.

In a particular embodiment, the impedance processor 140 generates the first and second impedance signals based on the current of the electric signals and the measured or sensed voltage of the resulting electric signals according to techniques well known in the art. In a particular embodiment, the first and second impedance signals are first and second cardiogenic impedance signals representative of the impedance as measured over a portion of the heart. In an alternative embodiment, the first and second impedance signals are first and second trans-thoracic impedance signals.

The first and second impedance signals are optionally a bandpassed version of the calculated impedance in order to remove or at least suppress the respiratory contribution to the impedance signals. In the case of cardiogenic impedance signals, the first and second impedance signals will not have any DC component, i.e. their respective average value is zero.

As known in the art, bipolar, tripolar or quadropolar impedance signals can be determined. In a bipolar setting the same pair of electrodes is used by both the signal generator 120 for signal application and the signal sensing unit 130 for sensing the resulting electric signals. Bipolar impedance signals are in particular reflective of the local environment around the electrodes. Tripolar settings have a common electrode for signal application and signal sensing, whereas quadropolar settings use two electrodes for signal application and two other electrodes for signal sensing. Tripolar and quadropolar impedance signals are more reflective of global properties affecting the impedance as compared to the bipolar impedance signals.

Non-limiting examples of suitable impedance vectors that can be employed according to the embodiments include a left ventricular (LV)—right atrial (RA) bipolar impedance vector using one electrode of a RA lead and one electrode of a LV lead to apply and sense electric signals. Another variant is to use a tripolar impedance vector where the electric signals are applied between one electrode of a right ventricular (RV) lead and the case electrode of an IMD and the resulting electric signals are sensed between the case electrode and another electrode of the RV lead.

If the signal generator 120 generates electric signals that are applied during multiple periods of normal hemodynamic status and in connection with multiple periods of abnormal hemodynamic status, the impedance processor 140 advantageously determines multiple sets of the first impedance signal, typically one such first impedance signal per period of normal hemodynamic status, and multiple sets of the second impedance signal, typically one such second impedance signal per period of abnormal hemodynamic status.

A parameter processor 150 of the system 100 is implemented to calculate first parameter values of a set of N different impedance-derivable parameters based on the first impedance signal. The parameter processor 150 correspondingly calculates second parameter values of the set of N different impedance-derivable parameters based on the second impedance signal. Hence, two different data sets are determined by the parameter processor 150; the first set corresponds to the impedance-derivable parameter values applicable during the period of normal hemodynamic status and the second set corresponds to the parameter values relevant to the period of abnormal hemodynamic status.

The set of N impedance-derivable parameters is a set of multiple, i.e. N≥2, predefined parameters that are derivable and can be calculated from the first and second impedance signals. Hereinafter follows a list of examples of such impedance-derivable parameters that can be used according to the embodiments. The listed impedance-derivable parameters should be seen as illustrative but preferred examples of such parameters that can be used according to the embodiments. The embodiments therefore encompass utilizing different combinations of N listed parameter values. As mentioned above N is equal to or larger than two but is advantageously at least three and is advantageously selected in the range of from 3 up to 15, preferably from 3 up to 10, such as from 5 to 10.

Average: This impedance-derivable parameter represents the average impedance value during a heart cycle in the first or second impedance signal.

Linear fit-correlation coefficient: This impedance-derivable parameter is a measure of how well the impedance during a heart cycle in the first or second impedance signal correlates to a defined impedance template acquired during normal conditions with normal hemodynamic status. The greater the difference between the current impedance waveform during the heart cycle and the impedance template, the lower the correlation coefficient will be.

Linear fit-gain: This impedance-derivable parameter is similar to the correlation coefficient above. It is calculated by comparing the current impedance waveform during a heart cycle in the first or second impedance signal with an impedance template obtained during normal condition with normal heart rhythm and normal hemodynamic status. However, instead of looking at the correlation coefficient, the average size of the current impedance waveform is studied. A linear approximation based on the impedance template is fitted to the current impedance waveform by minimizing the least square, min(|Z−template±×gain+offset|). In this embodiment, the current impedance waveform (Z) is fit to the impedance template (template) and the amount of amplification or attenuation (gain) determined in the fitting is employed as impedance-derivable parameter.

Max index: The time to the maximum impedance peak within the first 100 ms following an R wave in a heart cycle of the first or second impedance signal is an impedance-derivable parameter.

Fractionation: This impedance-derivable parameter is the length of the impedance waveform during a heart cycle for the first or second impedance signal after it has been normalized with regard to time and amplitude.

Characteristic rate: This impedance-derivable parameter is the characteristic or instantaneous rate for a heart cycle. It is preferably derivable from the first or second impedance signal using the Hilbert transform and is calculated by detrending data in a window by removing the average and linear trend from the data. The analytical signal of the detrended signal is calculated using the Hilbert function. The phase angle of the analytical signal is determined and corrected using an unwrap function, i.e. adding multiples of ±2π when absolute jumps between consecutive elements of the phase angle are greater than or equal to the default jump tolerance of π radians. This is the instantaneous phase. The instantaneous phase is low pass filtered, for instance by a running average of length 1 s and the low pass filtered phase is multiplied by ½π. The instantaneous rate is calculated for each sample of the first or second impedance signal according to above and is finally averaged for each heart cycle to get the characteristic rate.

Frequency integral parameter: A fast Fourier transform (FFT) is performed on the preceding 1 s of impedance data in the first or second impedance signal. The power at various frequencies is used to calculate the frequency integral parameter by finding an integral of the power at the frequencies.

Average crossings: This impedance-derivable parameter is simply the number of crossings of the first or second impedance signal over the average impedance during a heart cycle.

Peak to peak: The maximum impedance peak within the first 100 ms following an R wave in a heart cycle minus the minimum value occurring during the heart cycle but prior the maximum impedance peak in the first or second impedance signal is calculated.

Min index: The time of the minimum impedance peak occurring after the R wave but before the maximum impedance peak within the first 100 ms in the first or second impedance signal is calculated.

The above described impedance-derivable parameters have been tested in animal experiments, which are further described herein. There are though other impedance-derivable parameters that also could be used together with or instead of any of the above-described impedance-derivable parameters, such as curvature length of the first or second impedance signal during a heart cycle; mean, median or standard deviation of energy distribution calculated from the first or second impedance signal; systolic slope of the first or second impedance signal, etc.

The system 100 of FIG. 1 also comprises a model processor 160 configured to estimate N+1 coefficients of a linear parametric status model based on the first parameter values and the second parameter values of the N impedance-derivable parameters determined by the parameter processor 150. The linear parametric status model is defined as $$Index^j = c_0 + \sum_{i=1}^{N} c_i f_i^j,$$

where j=1, 2, $c_0$, $c_i$ represent the N+1 coefficients, $f_i^1$ represent the first parameter values, $f_i^2$ represent the second parameter values, $Index^1$ has a predefined first value representative of normal hemodynamic status of the subject and $Index^2$ has a predefined second value representative of abnormal hemodynamic status of the subject. Thus, the task of the model processor 160 is to estimate the values of the coefficients $c_o, c_1, \ldots, c_N$ using the first parameter values and the second parameter values. If the parameter processor 150 has, as previously discussed, determined multiple sets of first parameter values and multiple sets of second parameter values originating from different periods of normal and abnormal hemodynamic status, respectively, the model processor 160 preferably uses these sets of first and second parameter values when estimating the values of the coefficients for the linear parametric status.

$Index^1$ and $Index^2$ have predefined values that are defined to represent normal and abnormal hemodynamic status, respectively. For instance, a value of 100 could be employed for $Index^1$ to indicate normal hemodynamic status. Correspondingly, a value of 0 or 1 could be employed for $Index^2$ to indicate abnormal hemodynamic status. In an alternative embodiment, $Index^1=1$ and $Index^2=0$.

In these embodiments, a higher value of the hemodynamic status index represents a better or more normal hemodynamic status as compared to a lower value of the hemodynamic status index. In an alternative approach, a low value of the status index indicates normal hemodynamic status, whereas a high value of the status index instead signals abnormal hemodynamic status. In such a case, the above presented examples of values of $Index^1$ and $Index^2$ can basically be exchanged with each other.

The present embodiments are not limited to usage of any particular values of $Index^1$ and $Index^2$. However, once the predefined values of $Index^1$ and $Index^2$ have been selected they are employed throughout usage of the linear parametric status model and for the assessment of the hemodynamic status of the subject.

In a non-limiting example, the parameter processor 150 has determined three sets of first parameter values $f_1^1$, $f_2^1$, $f_3^1$, $f_4^1$, $f_1^{1'}$, $f_2^{1'}$, $f_3^{1'}$, $f_4^{1'}$ and $f_1^{1''}$, $f_2^{1''}$, $f_3^{1''}$, $f_4^{1''}$ and two sets of second parameter values $f_1^2$, $f_2^2$, $f_3^2$, $f_4^2$ and $f_1^{2'}$, $f_2^{2'}$, $f_3^{2'}$, $f_4^{2'}$. In this example, four different impedance-derivable parameters have been used, $Index^1$ set to 100 and $Index^2$ set to 1. The model processor 160 then determines the value of the coefficients $c_0$, $c_1$, $c_2$, $c_3$, $c_4$ from the equations:

$$100=c_0+c_1f_1^1+c_2f_2^1+c_3f_3^1+c_4f_4^1$$

$$100=c_0+c_1f_1^{1'}+c_2f_2^{1'}+c_3f_3^{1'}+c_4f_4^{1'}$$

$$100=c_0+c_1f_1^{1''}+c_2f_2^{1''}+c_3f_3^{1''}+c_4f_4^{1''}$$

$$1=c_0+c_1f_1^2+c_2f_2^2+c_3f_3^2+c_4f_4^2$$

$$1=c_0+c_1f_1^{2'}+c_2f_2^{2'}+c_3f_3^{2'}+c_4f_4^{2'}$$

The determination of the N+1 coefficients based on the input first and second parameter values can be performed according to prior art techniques for solving a system of equations, preferably an overdetermined system of equations. In the latter case, a least squares method or other optimization technique can be employed to find optimal values of the coefficients.

Figure 5:
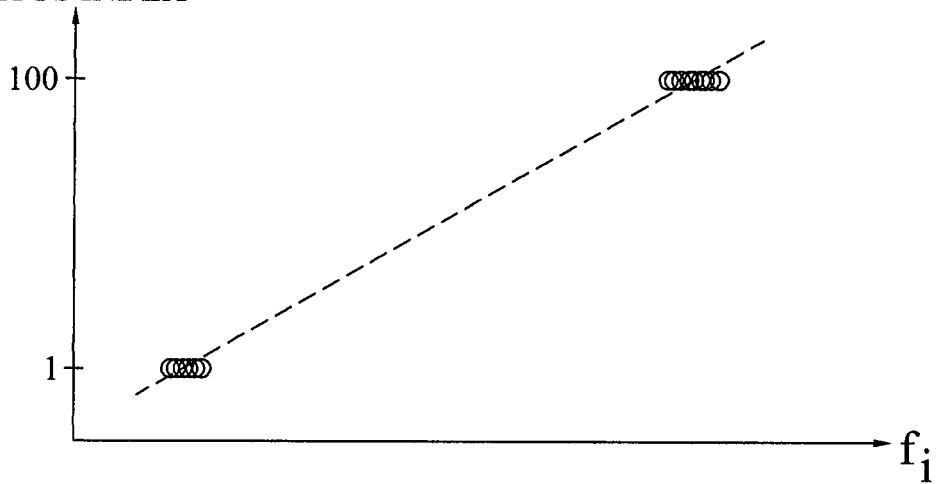
FIG. 5 is a diagram schematically illustrating determining a linear parametric status model according to an embodiment.

FIG. 5 visually illustrates this concept. The Y-axis of the diagram represents the hemodynamic status index with the first predefined value of 100 representing normal hemodynamic status of the subject and the second predefined value of 1 representing abnormal hemodynamic status. The X-axis represents the determined parameter value of one of the N impedance-derivable parameters. In practice, the diagram would be a N+1 dimensional diagram with one axis or dimension representing the hemodynamic status index and N dimensions or axes representing the N different impedance-derivable parameters.

Figure 6:
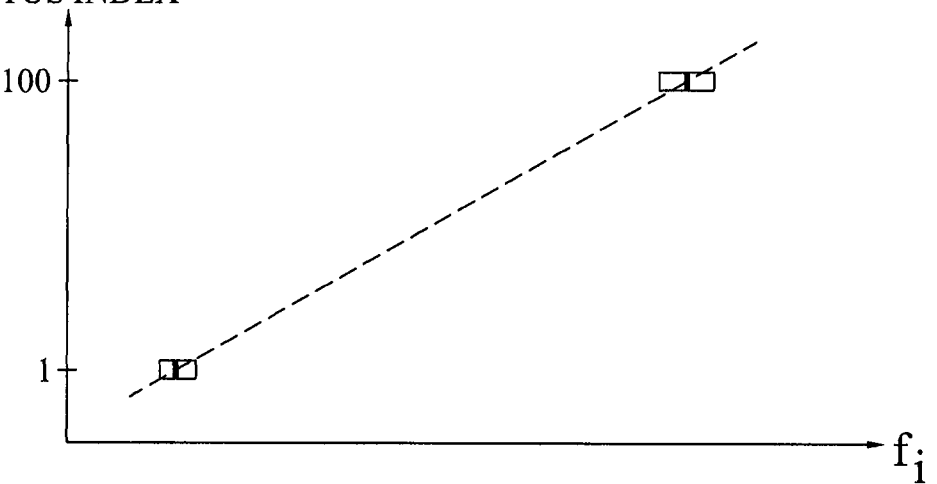
FIG. 6 is a diagram schematically illustrating a determined linear parametric status model according to an embodiment.

FIG. 5 illustrates first parameter values of the impedance-derivable parameter determined during different periods of normal hemodynamic status and second parameter values determined in connection with periods of abnormal hemodynamic status. In FIG. 6 the mean or average of the first and second parameter values are illustrated together with the standard deviation.

The N+1 coefficients determined by the model processor 160 are stored in a memory 170, see FIG. 1, of the system 100 as representations of the linear parametric status model determined for the given subject.

The linear parametric status model determined by the system 100 will be specific for the particular subject. This means that the coefficients of the linear parametric status model determined for a given subject will typically be very different from the coefficients determined for another subject even though the same predefined first and second values representative of normal and abnormal hemodynamic status are employed for the two subjects. This is a strength of the embodiments and makes the assessment of a subject's hemodynamic status much more reliable as compared to prior art population-general solutions.

The generation and application of electric signals by the signal generator 120 and the sensing of the resulting electric signals by the signal sensing unit 130 can be conducted according to various embodiments. In a particular embodiment, the signal generator 120 and the signal sensing unit 130 are configured to operate periodically or intermittently. The sensed "raw" electric signals can then be stored in the memory 170 or impedance signals are determined by the impedance processor 140 and then stored in the memory 170. In such a case, the raw signals or the impedance signals can be tagged with information defining whether the hemodynamic status was normal or abnormal, such as estimated based on other sensor inputs, such as a tachyarrhythmia detector 190 to be further described herein. Alternatively, the raw signals or the impedance signals can be tagged with information allowing identification of the time instance during which the signals were collected. In such a case, it is then later possible to identify the relevant signal samples that coincide with normal or abnormal hemodynamic status periods as determined based on feedback information from the subject. For instance, the subject can tell his/her physician that he/she experienced a period with rushing heart rhythm, possible causing the subject to faint or, if the subject has an implanted pacemaker, defibrillator, cardioverter or implanted cardioverter defibrillator (ICD), delivery of a defibrillation shock. The physician can then match this period of abnormal hemodynamic status to those impedance signal samples or raw electric signal samples that occurred during or at least close in connection with the experienced period with abnormal hemodynamic status.

Correspondingly, impedance signal samples or "raw" electric signal samples can be identified for periods in which the subject says that he/she felt fine or ok and therefore had normal hemodynamic status.

In these embodiments, the signal generator 120 and the signal sensing unit 130 operate independently of any detected medical conditions and then afterwards periods of normal or abnormal hemodynamic status are identified in order to identify the relevant samples in the determined impedance signal or in the resulting electric signals. An alternative approach, which generally saves more power or energy for the system 100, is to only apply electric signals and sense the resulting electric signals upon certain specific events or criteria. For instance, the periods of abnormal hemodynamic status may occur due to different medical conditions. An example of such a medical condition is a tachyarrhythmia event. The system 100 therefore optionally comprises a tachyarrhythmia detector 190 configured to generate a tachyarrhythmia signal in response to a detected tachyarrhythmia period or event. The tachyarrhythmia detector 190 preferably conducts the tachyarrhythmia detection based on electric signals sensed from the heart of the subject by at least one electric lead connectable to the lead connector 110. The tachyarrhythmia detector 190 can therefore be directly connected to the lead connector 110 or to the signal sensing unit 130 that registers sensed electric signals that are processed by the tachyarrhythmia detector 190 in order to detect any tachyarrhythmia event. The tachyarrhythmia detector 190 preferably performs such tachyarrhythmia detection according to prior art techniques, i.e.

generate the tachyarrhythmia signal if the current heart rate exceeds a predefined threshold, such as a heart rhythm that originates in the ventricles of the heart and produces a heart rate of at least 120 beats per minute.

In such a case, the signal generator 120 and optionally the signal sensing unit 130 can respond to the tachyarrhythmia signal. Thus, the signal generator 120 starts generating and applying the electric signals in response to the tachyarrhythmia signal and the signal sensing unit 130 correspondingly starts sensing the resulting electric signals. Thus, the electric signals applied and the resulting electric signals sensed in connection with periods of abnormal hemodynamic status can be applied and sensed in connection with a tachyarrhythmia event as detected by the tachyarrhythmia detector 190.

In an alternative embodiment, the periods of abnormal hemodynamic status do not correspond to all tachyarrhythmia events detected by the tachyarrhythmia detector 190. In this embodiment, only those tachyarrhythmia events requiring generation and application of defibrillation shocks to the subject are regarded as periods of abnormal hemodynamic status. The system 100 then preferably comprises an implantable medical device in the form of a pacemaker, defibrillator, cardioverter or ICD capable of generating such defibrillation shocks, which is further described herein.

The electric signal application and the resulting electric signal sensing in connection with periods of abnormal hemodynamic status for the purpose of generating the second impedance signals and the second parameter values of the impedance-derivable parameters are then advantageously conditioned to occur in connection to tachyarrhythmia events detected by the tachyarrhythmia detector 190 and requiring application of a defibrillation shock.

This further means that any tachyarrhythmia event that is not treated by a defibrillation shock and regarded as being less severe do not qualify as periods of abnormal hemodynamic status. The tachyarrhythmia may spontaneously revert back to normal heart rhythm or is combated with other treatment strategies, such as anti-tachyarrhythmia pacing.

Correspondingly, the system 100 can instead or additionally be equipped to detect periods of vasovagal syncope and/or transient ischemic attacks that cause abnormal hemodynamic status to the subject. Such detections are then performed according to prior art techniques. For instance, vasovagal syncope detection can be performed as disclosed in U.S. Pat. Nos. 5,284,491 or 5,676,686, the teaching of which with regard to vasovagal syncope detection is incorporated herein by reference. For instance, vasovagal syncope can be detected as a drop in the subject's heart rate below a lower hysteresis rate and by determining whether the average rate of decrease in the heart rate, over a defined number of heart cycles or a defined time interval prior to reaching the hysteresis rate, is greater than a preset value. Alternatively, vasovagal syncope can be detected by detecting a rapid drop in spontaneous heart rate depolarization and determining whether the spontaneous heart depolarization rate has dropped more than a defined amount from a highest persistent heart rate over a limited time interval.

Periods of normal hemodynamic status can be determined to be periods during which the subject had normal cardiac rhythm. The signal generator 120 can then be conditioned to start the application of electric signal during periods of normal hemodynamic status based on feedback signals indicating that the current cardiac rhythm is within the normal range as determined by the signal sensing unit 130 or a cardiac rhythm detecting unit (not illustrated) of the system 100.

In the discussion above, the system 100 basically employs two different sets of parameter values in order to estimate the linear parametric status: first parameter values corresponding to normal hemodynamic status and second parameter values corresponding to abnormal hemodynamic status. These two sets can be accompanied by at least one additional set corresponding to normal hemodynamic status but during physical activity of the subject. For instance, a bicycle ergometer, i.e. a stationary exercise bicycle with an ergometer to measure the work done by the subject, could be used when conducting the measurements in connection with physical activity. The load can thereby be set accurately to get a better defined level of physical activity.

In such a case, the signal generator 120 applies electric signals and the signal sensing unit 130 senses resulting electric signals also during periods of normal hemodynamic status and physical activity. The impedance processor 140 calculates a third impedance signal based on the resulting electric signals and the applied signals. The parameter processor 150 processes this third impedance signal in order to determine third parameter values of the N impedance-derivable parameters and the model processor 160 also employs these third parameter values when estimating the linear parametric status. In such a case, the hemodynamic status index for the third parameter values could have the predefined value of 120 if the first predefined value is 100 and the second predefined value is 0 or 1 as discussed in the foregoing.

The impedance signals determined by the impedance processor 140 are typically dependent on the posture of the subject. In a particular embodiment, the system 100 therefore comprises or is connectable to a posture sensor 192 configured to generate a posture signal representative of a current posture of the subject.

In an embodiment, the signal generator 120 is configured to generate electric signals only when the subject is in a predefined target posture as indicated by the posture signal from the posture sensor 192. Thus, in this embodiment, the first and second impedance signals are determined during periods of normal and abnormal hemodynamic status, respectively, and when the subject is in the predefined target posture. Examples of such predefined target postures could be supine position, i.e. lying down with the face up, standing upright and lying down on the left or right side. In an embodiment, the predefined target posture is standing upright and in another embodiment it is the supine position.

Limiting the determination of the N+1 coefficients to input data derived from a same predefined target posture will enhance the specificity and reliability of the linear parametric status model.

In an alternative approach with enhanced reliability, the system 100 determines at least two linear parametric status models, where each such model is specific for a predefined target posture of the subject. For instance, a first linear parametric status model can be determined for an upright posture whereas a second linear parametric status model is determined for a supine posture. The first linear parametric status model will then be applicable, as is further discussed herein, for assessment of the subject's current hemodynamic status when the subject is standing, whereas the second linear parametric status model can correspondingly be employed when the subject is lying down with the face up.

The signal generator 120 is, in this embodiment, configured to generate and apply electric signals during periods of normal hemodynamic status and when the subject is in the first predefined posture and when the subject is in the second predefined posture as determined by posture signals from the posture sensor 192. Correspondingly, the signal generator 120 generates and applies electric signals in connection with periods of abnormal hemodynamic status and when the subject is in the first predefined posture and when the subject is in the second predefined posture.

The signal sensing unit 130 senses the resulting electric signals during the periods of normal and abnormal hemodynamic status when the subject is in the first predefined posture and when the subject is in the second predefined posture. The impedance processor 140 determines, in this embodiment, at least four impedance signals. The first impedance signal corresponds to the impedance during normal hemodynamic status and the first predefined posture and the second impedance signal is the impedance during abnormal hemodynamic status and the first predefined posture. A third impedance signal reflects the impedance during normal hemodynamic status but in the second predefined posture. Finally, a fourth impedance signal corresponds to the impedance during abnormal hemodynamic status and the second predefined posture.

The parameter processor 150 calculates first, second, third and fourth parameter values of the set of N impedance-derivable parameters based on the first, second, third and fourth impedance signals, respectively. The first and second parameter values from the parameter processor 150 are input to the model processor 160 in order to estimate N+1 coefficients of a first linear parametric status model $$Index_1^j = c_0 + \sum_{i=1}^{N} c_i f_i^j,$$

where $j=1, 2$, $c_0$, $c_i$ represent the N+1 coefficients, $f_i^1$ represent the first parameter values, $f_i^2$ represent the second parameter values, $Index_1^1$ has the predefined first value representative of normal hemodynamic status of the subject and $Index_1^2$ has the predefined second value representative of abnormal hemodynamic status of the subject. Correspondingly, the third and fourth parameter values from the parameter processor 150 are employed by the model processor 160 in order to estimate N+1 coefficients of a second linear parametric status model $$Index_2^j = d_0 + \sum_{i=1}^{N} d_i g_i^j,$$

where $j=1, 2$, $d_0$, $d_i$ represent the N+1 coefficients, $g_i^1$ represent the third parameter values, $g_i^2$ represent the fourth parameter values, $Index_2^1$ has the predefined first value representative of normal hemodynamic status of said subject and $Index_2^2$ has the predefined second value representative of abnormal hemodynamic status of the subject.

The determination of the 2(N+1) coefficients of the two linear parametric status models is basically conducted as previously discussed herein. These determined coefficients are stored in the memory 170 as representations of the first and the second linear parametric status models. The system 100 will then have access to two linear parametric status models that are adapted for two different subject postures and can be employed to assess the hemodynamic status of the subject either when the subject is in the first predefined posture (the first linear parametric status model) or in the second predefined posture (the second linear parametric status model).

The above described embodiment can, of course, be extended to the case of determining three of more different linear parametric status models that are adapted for three or more different postures of the subject.

The posture sensor 192 of the system 100 can be designed according to any prior art posture sensor technique, including, for instance, microelectromechanical systems (MEMS) based posture sensors.

It is optionally possible for the system 100 to update the linear parametric status model after some period of time to reflect changes to the impedance signal that do not depend on the hemodynamic status of the subject. For instance, following implantation of an implantable medical lead with electrodes, connective tissue will grow around and at least partly encapsulate the electrodes. This encapsulation or maturization of an electrode will cause changes in the impedance signal if the electrode is employed for applying electric signals and/or sensing the resulting electric signals.

Figure 8:
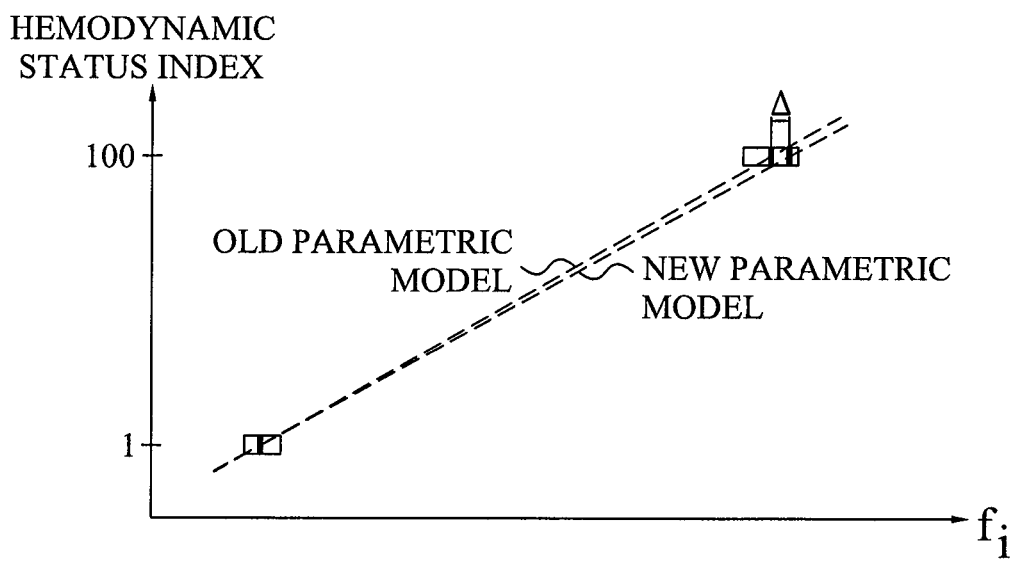
FIG. 8 is a diagram schematically illustrating updating a linear parametric status model according to an embodiment.

The linear parametric status model can therefore be updated to adjust to such changes that are not caused by changes in the hemodynamic status of the subject. The updating of the hemodynamic status is basically conducted in the same way as when generating the linear parametric status model as described herein. However, in such a case both previously determined parameter values or the previously determined coefficients and newly calculated parameter values can be employed when determining updated values of the N+1 coefficients of the linear parametric status model. This concept is visually illustrated in FIG. 8. An indication of the need to update the linear parametric status model is if there is a shift in the hemodynamic status index during periods of normal hemodynamic status, as reflected by $\Delta$ in FIG. 8. These shifts or changes in the hemodynamic status are, however, rather slow over time in clear contrast to changes in the hemodynamic status of the subject, which are noted as abrupt and very rapid changes in the hemodynamic status index. It is also possible to conduct the updating of the hemodynamic status model automatically. Any shift in models can be of diagnostic value and can therefore be trended for diagnostic purposes.

The need to update the linear parametric status model is typically determined by the subject's physician based on the trend in previously calculated hemodynamic status indices obtained using the linear parametric status model. Thus, if there is slow drift in the status indices, this indicates a need to update the linear parametric status model. The physician then advantageously controls the system 100 to initiate an updating of the linear parametric status.

In the above described embodiment an impedance sensor is employed to generate impedance signals from which impedance-derivable parameters can be extracted in order to generate a hemodynamic status model. The impedance sensor is then represented by the impedance processor, the signal generator and the signal sensing unit. Impedance-based embodiments have the advantage that no dedicated sensor equipment is needed. In clear contrast, any electrodes and leads already connectable to the system and signal generating and signal sensing unit that are typically already present in the system can be reused to generate the hemodynamic status model.

The embodiments are, however, not limited to such impedance sensors and the generation of a set of N different impedance-derivable parameters. In alternative embodiments, the system comprises or is connectable, typically through the lead or sensor connector, to at least one sensor configured to generate a sense signal representative of a characteristic or property sensed from the subject, preferably from the subject's heart or vascular system. Examples of such sensors include blood pressure sensors configured to sense the blood pressure of the subject and generate a sense signal representative of the sensed blood pressure. Other examples include 3D accelerometers configured to monitor the motion of the subject's heart during heart cycles, i.e. diastole and systole. The sense signal then represents such monitored heart motion and in particular represents the longitudinal and radial motion of the heart. Monitoring of the heart's motion and dimension can also be performed by implantable motion sensors. Microphones and accelerometers that are arranged for detecting vibrations originating from the heart can also be used as sensors. The sensor does not necessarily have to be limited to perform cardiac monitoring but can be provided in the vascular system of the subject, such as in the aorta or the arteria pulmonalis.

In such a case, the system comprises the lead connector connectable to at least one sensor, typically provided on a lead structure. The sensor monitors a characteristic of the subject and generates a sense signal. The sensor thereby generate a first sense signal during a period of normal hemodynamic status of the subject and a second sense signal in connection with a period of abnormal hemodynamic status of the subject. The parameter processor calculates first parameter values of the set of N different sensor-derivable parameters based on the first sense signal and calculates second parameter values of the set of N different sensor-derivable parameters based on the second sense signal. The calculation of the N different sensor-derivable parameters from the first and second sense signals can basically be conducted as previously described above for the first and second impedance signals.

The embodiments can, thus, use any of the above described sensors as an alternative to the impedance sensor. Alternatively, multiple different sensors can be used together, such as the impedance sensor and at least one other sensor. The linear parametric status model could then be estimated by the model processor as $$Index^j = c_0 + \sum_{i=1}^{N}(c_i f_i^j + b_i h_i^j),$$

where $j=1, 2$, $c_0$, $c_i$, $b_i$ represent $2N+1$ coefficients to be determined, $f_i^1$ represent the first parameter values calculated from the first impedance signal, $f_i^2$ represent the second parameter values calculated from the second impedance signal, $h_i^1$ represent the first parameter values calculated from the first sense signal, $h_i^2$ represent the second parameter values calculated from the second sense signal, $Index^1$ has the predefined first value representative of normal hemodynamic status of the subject and $Index^2$ has the predefined second value representative of abnormal hemodynamic status of the subject.

With reference to FIG. 1, once the system 100 has determined at least one linear parametric status model that is specific for the given subject according to any of the previously described embodiments, the parametric status model can be employed to assess the hemodynamic status of the subject. During such a status assessment period the signal generator 120 generates and applies electric signals over two electrodes connectable to the lead connector 110. The signal sensing unit 130 correspondingly senses the resulting electric signals during this status assessment period. The impedance processor 140 determines an impedance signal based on the electric signals applied and the resulting electric signals sensed during the status assessment period. The impedance signal is processed by the parameter processor 150 in order to calculate parameter values of the set of N different impedance-derivable parameters. The operations of these units 120-150 of the system 100 are, thus, basically the same as during the periods of normal/abnormal hemodynamic status in terms of providing parameter values. The difference being that now the system 100 and its linear parametric status model is employed in order to assess a current hemodynamic status of the subject whereas previously the system 100 was employed in order to generate the linear parametric status model and the hemodynamic status of the subject was known.

The determined parameter values are input to a status processor 180 together with the N+1 coefficients of the linear parametric status model retrieved from the memory 170. The status processor 180 thereby calculates an index representative of the current hemodynamic status of the subject based on the N+1 coefficients and the N parameter values. In a typical embodiment, the index will be in the interval between the first predefined value representing normal hemodynamic status and the second predefined value representing abnormal hemodynamic status.

The calculated hemodynamic status index is advantageously forwarded to a threshold comparator 182 configured to compare the hemodyanmic status index with at least one threshold value. This threshold value is preferably smaller than the first predefined value representing normal hemodynamic status but larger than the second predefined value representing abnormal hemodynamic status.

The threshold value can then be selected to differentiate between normal or healthy subject status and a hemodynamic status that is not regarded as being normal and for which combative actions should be taken. For instance, if the first predefined value representing normal hemodynamic status is set to 100 and the second predefined value representing abnormal hemodynamic status is set to 0 or 1, the threshold value could be set to 50. This means that for those assessment periods during which the hemodynamic status index determined for the subject based on the linear parametric status model exceeds 50 the subject is regarded as being healthy or at least not that ill that further actions need to be taken. If the hemodynamic status index, however, falls below 50 the current situation is so bad or could potentially lead to a dangerous or even life-threatening situation that actions should be taken.

In an alternative embodiment, the threshold comparator 182 has access to multiple predefined threshold values. The particular action to be taken, if any, is then dependent on whether the current hemodynamic status index exceeds or is below any of the multiple threshold values. Examples of suitable actions to be taken could then be to inform the subject of a potential abnormal hemodynamic status and/or inform the subject's physician of the potential abnormal hemodynamic status, trigger a combating pacing scheme and trigger delivery of defibrillation shocks. These actions could then be associated with different threshold values. Thus, if the current hemodynamic status index exceeds the first threshold value, no actions need to be taken. If the status index instead is below the first threshold value but exceeds the second threshold value, the subject and/or the physician is informed of the potential abnormal hemodynamic status. Instead of alerting the subject and the physician, the device can be set to an alert state to be ready to apply any therapy if needed. For instance, an implantable medical device incorporating the system or a portion thereof could start charging its shock generator for delivery of a defibrillation shock, though not yet delivering the shock to the subject. If the status index instead would be smaller than the second threshold but exceeds the third threshold value, combating pacing pulses, such as anti-tachyarrhythmia pacing pulses are applied to the subject. Finally, if the status index is even lower than the third threshold value, the hemodynamic status is really poor and potentially life-threatening so that defibrillation shocks should be applied to the subject.

The hemodynamic status model as described above can be used together with other diagnostic parameters and techniques, such as traditional tachyarrhythmia detectors, in order to assess the hemodynamic status of the subject and in particular when discriminating whether to apply combating therapy to the subject.

Figure 7:
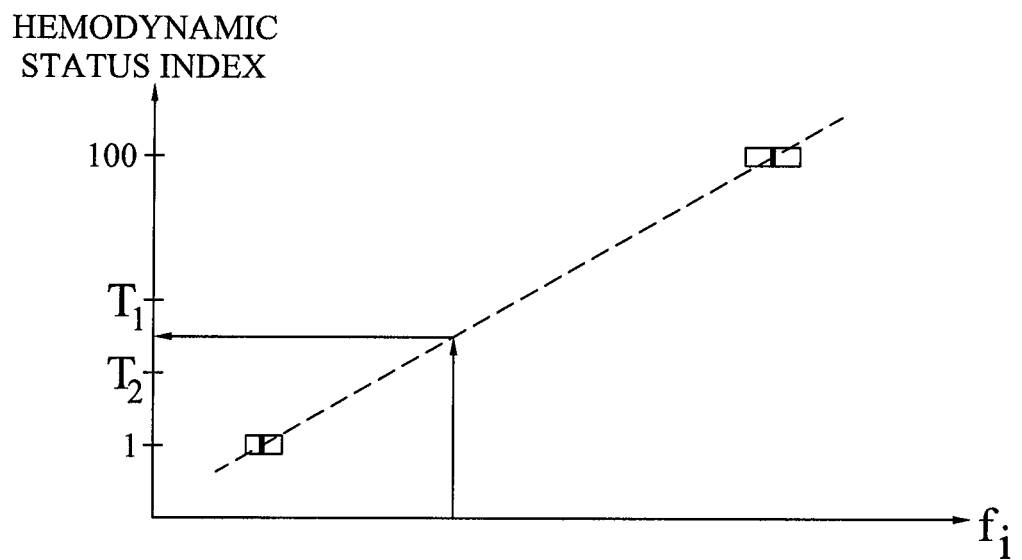
FIG. 7 is a diagram schematically illustrating determining a hemodynamic status index based on a linear parametric status model according to an embodiment.

FIG. 7 schematically illustrates the concept of using threshold comparisons. Thus, the current parameter values of the set of N impedance-derivable parameter values are input in the linear parametric status model to output a current hemodynamic status index. This status index can then be compared to one or more threshold values, $T_1$, $T_2$, in order to determine which action, if any, to take for the subject and the current situation.

In an optional embodiment, the system 100 therefore comprises a therapy selector 184, see FIG. 1, that is configured to select a particular therapy or action for the subject based on the comparison conducted by the threshold comparator 182. The therapy selector 184 then advantageously generates a therapy signal representative of the proposed therapy. For instance, the therapy signal can trigger an alarm unit (not illustrated) of the system 100 to run an audio and/or tactile alarm that indicates to the subject that he/she currently has a potentially abnormal hemodynamic status as assessed based on the linear parametric status model. Correspondingly, the therapy signal can trigger activation of an alert state, such as charging for a defibrillation shock. Alternatively, or in addition, a transmitter or transceiver (not illustrated) of the system 100 can transmit an alarm signal to the physician using a wired or wireless communication network to thereby inform the physician of the potential abnormal hemodynamic status of the subject. The alarm then comprises information allowing the physician to identify the subject and information of what type of alarm that is generated.

The therapy signal can also trigger the signal generator 120 or a dedicated pacing pulse generator (not illustrated) of the system 100 to generate and apply pacing pulses to the subject's heart in order to combat the abnormal hemodynamic status. An example of such pacing pulses to be applied is to combat tachyarrhythmias that are regarded to not be so severe or life-threatening that they require defibrillations. For instance, the tachyarrhythmia could be a so-called hemodynamically stable tachycardia that might be more appropriately treated by applying low-voltage anti-tachyarrhythmia pacing instead of defibrillation. If the hemodynamically stable tachycardia is of ventricular origin, then anti-tachyarrhythmia pacing can be applied in the ventricle or if the hemodynamically stable tachycardia is of atrial origin, such as supravetnricular tachycardia, then an atrial anti-tachyarrhythmia pacing might be appropriate.

The therapy signal could alternatively trigger the signal generator 120 or a dedicated defibrillation pulse generator (not illustrated) of the system 100 to generate and apply one or more defibrillation pulses or shocks to the subject's heart in order to combat really severe abnormal hemodynamic statuses.

If the system 100 has determined multiple different linear parametric status models for the subject, the posture sensor 192 is preferably activated during the status assessment period when the electric signals are applied and the resulting electric signals are sensed in order to determine the current posture of the subject during the status assessment period. The posture sensor 192 then generates a posture signal representative of the posture of the subject and forwards this posture signal to the status processor 180. The status processor 180 employs the posture signal in order to identify which linear parametric status model and which set of N+1 coefficients to use when calculating the hemodynamic status index for the current status assessment period.

Alternatively, if the system 100 has only determined a single linear parametric status model that is applicable for a given posture of the subject, the posture signal from the posture sensor 192 could control the system 100 to merely conduct a status assessment when the subject is in a posture for which the linear parametric status has been determined.

If the system employs at least one other sensor besides or in addition to the impedance sensor for generating the hemodynamic status model, that at least one sensor is used instead of or in addition to the impedance sensor during the assessment period in order to provide a sense signal, based on which sensor-derivable parameter values are calculated and input to the hemodynamic status model to assess the current hemodynamic status of the subject.

FIGS. 2 and 3 illustrate examples of implementation embodiments for the system 100 for determining a hemodynamic status model. In FIG. 2, the system 100 comprises an implantable medical device (IMD) 300 exemplified by a pacemaker, defibrillator, cardioverter or ICD. The IMD 300 is, in operation, connected to implantable medical leads 20, 30 having electrodes 22, 24, 26, 32, 34 in or in connection with the subject's 10 heart 15. The system 100 also comprises a non-implantable data processing unit 200, which could be, for instance, a physician's programmer, a computer, including lap top, part of a home monitoring device or system, etc. The non-implantable data processing unit 200 is capable of conducting wireless communication with the IMD 300, for instance RF-based communication. In such a case, the non-implantable data processing unit 200 comprises the required transmitter and receiver, or transceiver, equipment together with antenna in order to enable the wireless communication. Alternatively, the non-implantable data processing unit 200 could be connected, typically with a wired connection, to a communication device 210 that handles the communication with the IMD 300 on behalf of the non-implantable data processing unit 200. The required transmitter/receiver or transceiver equipment and antenna are then provided in or connected to the communication device 210 that operates similar to a base station for the non-implantable data processing unit 200.

With such an implementation embodiment of the system 100, the devices and functions of the system 100 as described in the foregoing in connection with FIG. 1 can be distributed among the IMD 300 and the non-implantable data processing unit 200. In an embodiment, the IMD 300 comprises the lead connector 110, the signal generator 120, the signal sensing unit 130, the impedance processor 140 and the memory 170 of FIG. 1. The IMD 300 also comprises a transmitter/receiver or transceiver with connected antenna configured to transmit data, such as data packets, representative of or carrying the first impedance signal and the second impedance signal determined by the impedance processor 140. The non-implantable data processing unit 200 then comprises the parameter processor 150 and the model processor 160 of FIG. 1. The transmitter/receiver or transceiver of or connected to the non-implantable data processing unit 200 receives the first and second impedance signals from the IMD 300 and generates the linear parametric status model based on this received data. In a preferred embodiment, the transmitter/receiver or transceiver also transmits the calculated coefficients of the linear parametric status model to the IMD 300 for storage therein in the memory 170.

In this implementation embodiment, the IMD 300 collects the basic data required to determine the linear parametric status model. The further processing of this data and the determination of the linear parametric status model is conducted in the non-implantable data processing unit 200. In contrast to the battery-driven IMD 300, the non-implantable data processing unit 200 generally has access to unlimited power by either being connected to a power point or socket or being powered by a rechargeable battery. Additionally, the non-implantable data processing unit 200 typically has superior processing capability as compared to the IMD 300, which is physically limited in size to include all equipment to function as an autonomous unit implanted in the subject's body. The processing capability of the IMD 300 is, hence, limited by the physical constraints of the IMD 300 and the limited power available from the battery of the IMD 300. The non-implantable data processing unit 200 is therefore generally better designed as compared to the IMD 300 to perform data processing and optimization required to determine the linear parametric status.

In an alternative implementation example, the IMD 300, in addition to the lead connector 110, the signal generator 120, the signal sensing unit 130 and the impedance processor 140, also comprises the parameter processor 150 and the memory 170. The IMD 300 thereby determines the first and second parameter values of the set of N impedance-derivable parameters and transmits data representative of or data packets carrying these first and second parameter values to the non-implantable data processing unit 200. The model processor 160 is in this embodiment implemented in the non-implantable data processing unit 200 to estimate the coefficients of the linear parametric status model based on the data received from the IMD 300. Data representative of or data packets carrying the coefficients of the linear parametric status model is transmitted to the IMD 300 for storage therein in the memory 170.

The optional devices of FIG. 1, i.e. the posture sensor 192, the tachyarrhythmia detector 190, the status processor 180, the threshold comparator 182 and the therapy selector 184 are preferably also implemented in the IMD 300 in these embodiments.

FIG. 3 illustrates an alternative implementation example for the system 100. In this embodiment the system 100 does not comprise any IMD 300. Instead the system 100 comprises a non-implantable data processing unit 200 in which the signal generator 120, the signal sensing unit 130, the impedance processor 140, the parameter processor 150, the model processor 160 and the memory 170 are implemented. The non-data processing unit 200 also comprises the lead connector 110 or is connected to a dedicated lead interface 220 in which the lead connector 110 is implemented as illustrated in FIG. 3. The lead connector 110 is in operation connected to leads 40, 50 having electrodes 42, 52 that are placed on the skin surface of the subject 10.

The above described implementation example for the system 100 illustrated in FIG. 3 is in particular advantageous for usage in a healthcare facility by a physician to determine linear parametric status models for the physician's patients.

Another implementation example of the system 100 merely involves the IMD 300 and not any non-implantable data processing unit. In such a case, all the devices of the system 100 are implemented in the IMD 300 that collects the raw data, processes it and determines the linear parametric status model from the processed data.

The devices 110 to 192 of the system 100 can be implemented in hardware or at least partly in software. Generally, the lead connector 110, the signal generator 120 and the memory 170 are provided as hardware-implemented devices. The other devices can also be provided in hardware or are implemented in software. The software includes computer program code elements or software code portions effectuating the operation of the devices. The program may be stored in whole or part, on or in one or more suitable volatile computer readable media or data storage means. The software may be loaded into the operating memory for execution by a processor. The computer/processor does not have to be dedicated to only execute the above-described functions but may also execute other software tasks.

Figure 4:
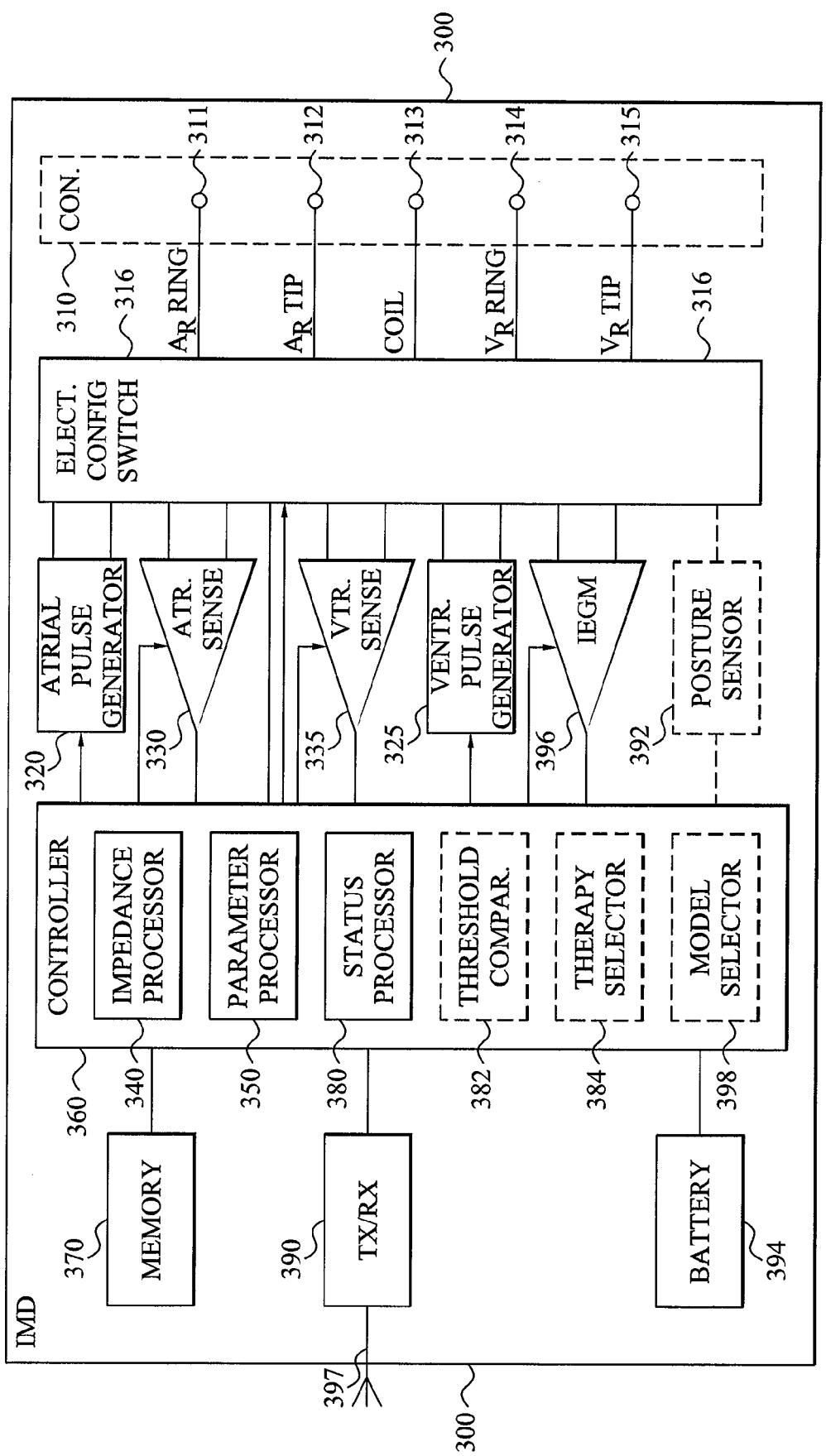
FIG. 4 is a schematic block diagram of an implantable medical device according to an embodiment.

FIG. 4 is a schematic block diagram of an IMD 300 according to an embodiment. FIG. 4 is a simplified block diagram depicting various components of the IMD 300. While a particular multi-chamber device is shown, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination.

The IMD 300 comprises a housing, often denoted as can or case in the art. The housing can act as return electrode (case electrode) for unipolar leads, which is well known in the art. The IMD 300 also comprises a lead connector 310 having, in this embodiment, a plurality of terminals 311-315. The terminals 311-315 are configured to be connected to matching electrode terminals of implantable medical leads connectable to the IMD 300 and the lead connector 310. FIG. 4 illustrates an embodiment with terminals 311-315 that corresponds to the IMD embodiment as illustrated in FIG. 2, i.e. having a right atrial lead 30 with a tip electrode 32 and a ring electrode 34 and a right ventricular lead 20 with a tip electrode 22, a ring electrode 24 and a defibrillation coil 26. If other lead embodiments are employed, the terminals of the lead connector 310 are appropriately modified to match the electrode terminals of the at least one connectable implantable medical lead.

If the IMD 300 is connectable to an atrial lead, the IMD 300 comprises an atrial pulse generator 320 generating pacing pulses for delivery by the atrial lead(s) preferably through an electronic configuration switch 316. The IMD 300 preferably also comprises a ventricular pulse generator 325 that generates pacing pulses for delivery by the ventricular lead(s) to the left and/or right ventricle.

It is understood that in order to provide stimulation therapy in different heart chambers, the atrial and ventricular pulse generators 320, 325 may include dedicated, independent pulse generators, multiplexed pulse generators, or shared pulse generators. The pulse generators 320, 325 are controlled by a controller 360 via appropriate control signals, respectively, to trigger or inhibit the stimulating pulses.

The controller 360 of the IMD 300 is preferably in the form of a programmable microcontroller 360 that controls the operation of the IMD 300. The controller 360 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 360 is configured to process or monitor input signal as controlled by a program code stored in a designated memory block. The type of controller 360 is not critical to the described implementations. In clear contrast, any suitable controller may be used that carries out the functions described herein. The use of microprocessor-based control circuits for performing timing and data analysis functions are well known in the art.

The optional electronic configuration switch 316 includes a plurality of switches for connecting the desired terminals 311-315 to the appropriate I/O circuits, thereby providing complete electrode programmability. Accordingly, the electronic configuration switch 316, in response to a control signal from the controller 360, determines the polarity of the stimulating pulses (e.g. unipolar, bipolar, combipolar, etc.) by selectively closing the appropriate combination of switches (not shown) as is known in the art.

An optional atrial sensing circuit or detector 330 and a ventricular sensing circuit or detector 335 are also selectively coupled to the atrial lead(s) and the ventricular lead(s) through the switch 316 for detecting the presence of cardiac activity in the heart chambers. Accordingly, the atrial and ventricular sensing circuits 330, 335 may include dedicated sense amplifiers, multiplexed amplifiers, or shared amplifiers. The switch 316 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 330, 335 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 330, 335 are connected to the controller 360, which, in turn, is able to trigger or inhibit the atrial and ventricular pulse generators 320, 325, respectively, in a demand fashion in response to the absence or presence of cardiac activity in the appropriate chambers of the heart.

Furthermore, the controller 360 is also typically capable of analyzing information output from the sensing circuits 330, 335 and/or an IEGM (intracardiac electrogram) unit 396 to determine or detect whether and to what degree tissue capture has occurred and to program a pulse, or pulse sequence, in response to such determinations. The sensing circuits 330, 335, in turn, receive control signals over signal lines from the controller 360 for purposes of controlling the gain, threshold, polarization charge removal circuitry, and the timing of any blocking circuitry coupled to the inputs of the sensing circuits 330, 335 as is known in the art.

Cardiac signals are applied to inputs of the IEGM unit 396 connected to the lead connector 310. The IEGM unit 396 is preferably in the form of an analog-to-digital (N/D) data acquisition unit configured to acquire IEGM signals, convert the raw analog data into a digital signal, and store the digital signals for later processing and/or transmission to a programmer by a transmitter or transceiver 390. The IEGM unit 396 is coupled to the atrial lead and/or the ventricular lead through the switch 316 to sample cardiac signals across any pair of desired electrodes.

Advantageously, the operating parameters of the IMD 300 may be non-invasively programmed into the memory 370 through a receiver or transceiver 390 in communication via a communication link with the previously described communication unit of the programmer. The controller 360 activates the transceiver 390 with a control signal. The transceiver 390 can alternatively be implemented as a dedicated receiver and a dedicated transmitter connected to separate antennas or a common antenna, preferably a radio frequency (RF) antenna 397.

The IMD 300 additionally includes a battery 394 that provides operating power to all of the circuits shown in FIG. 4.

According to the embodiments, the IMD 300 employs the atrial pulse generator 320 and/or the ventricular pulse generator 325 to generate, during a status assessment period, electric signals applicable over two electrodes connected to the lead connector 310. The electric signals are sub-threshold signals employed to generate impedance signals as compared to the traditional pacing pulses generated by the atrial and ventricular pulse generators 320, 325 that should be above the capture threshold. Alternatively, the IMD 300 could be equipped with a dedicated signal generator (not illustrated) in addition to the atrial and ventricular pulse generators 320, 325.

The atrial signal sensing unit 330 and/or the ventricular sensing unit 335 is configured to sense, during the status assessment period, resulting electric signals over two electrodes connected to the lead connector 310. Alternatively, a dedicated signal sensing unit (not illustrated) can be implemented in the IMD 300 for conducting this signal sensing.

The IMD 300 also comprises the previously described impedance processor 340 configured to determine an impedance signal based on the electric signals applied by the atrial and/or ventricular pulse generator 320, 325 and the resulting electric signals sensed by the atrial and/or ventricular sensing unit 330, 335 during the assessment period. A parameter processor 350 processes the impedance signal as previously described in order to calculate parameter values of the set of N impedance-derivable parameters. The calculated parameter values are input to a status processor 380 configured to calculate a hemodynamic status index representative of a current hemodynamic status of the subject in which the IMD 300 is implanted. The status processor 380 calculates the hemodynamic status index based on the input parameter values and N+1 coefficients of a linear parametric status model $$\text{Index} = c_0 + \sum_{i=1}^{N} c_i f_i,$$

wherein $c_0$, $c_i$ represent the N+1 coefficients and $f_i$ represent the parameter values calculated by said parameter processor 350.

The N+1 coefficients of the linear parametric status model are preferably retrieved from the memory 370 of the IMD 300. The coefficients can previously have been at least partly determined by the IMD 300 as described herein, in which the IMD 300 constitutes or forms part of the system for determining the hemodynamic status model. Alternatively, the coefficients can have been determined by a non-implantable data processing unit of the system and then transmitted to the transceiver 390 of the IMD 300 for storage in the memory 370.

In a preferred embodiment, the IMD 300 comprises a threshold comparator 382 configured to compare the hemodynamic status index calculated by the status processor 380 with at least one threshold. The operation of the threshold comparator 382 is the same as previously discussed above in connection with FIG. 1 and is therefore not further described herein. The IMD 300 may optionally also comprise a therapy selector 384, which basically operate as previously described in connection with FIG. 1 in order to generate a therapy signal representative of a proposed therapy for the subject based on the result of the comparison of the hemodynamic status index with the at least one threshold as determined by the threshold comparator 382. The therapy signal can be forwarded to the controller 360 to cause the controller 360 to trigger the atrial and/or ventricular pulse generator 320, 325 to generate and apply a pacing therapy, such as anti-tachyarrhythmia pacing, selected based on the therapy signal. The therapy signal can alternatively cause the controller 360 to trigger the atrial and/or pulse generator 320, 325 to generate a defibrillation shock to be applied to the subject's heart. Alternatively, the IMD 300 has a dedicated shock generator (not illustrated), which is controlled by the controller 360 based on the therapy signal. A further variant, as previously discussed, is that the controller 360 controls an alarm unit (not illustrated) of the IMD 300 to trigger an acoustic and/or tactile alarm based on the therapy signal. A further variant is also to generate an alarm message or call that is forwarded to the non-implantable data processing unit via the transceiver 390 in response to the therapy signal.

In an optional embodiment, the IMD 300 comprises a posture sensor 392 configured to generate a posture signal representative of a current posture of the subject. The posture signal is forwarded to the controller 360 and employed to control the generation of the hemodynamic status index. For instance, the controller 360 can control the atrial and/or ventricular pulse generator 320, 325 to generate the electric signals during the assessment period only when the subject is in a predefined target posture as indicated by the posture signal. In an alternative approach, the IMD 300 has access to multiple linear parametric status models that are applicable to different subject postures. The memory 370 then stores the N+1 coefficients for each such parametric status model. The IMD 300 optionally comprises a dedicated model selector 398 or the functions of this model selector 398 are conducted by the status processor 380. In either case, the posture signal from the posture sensor 392 is employed by the model selector 398 or the status processor 380 to identify the correct linear parametric status model to use based on the subject's current posture as indicated by the posture signal. The posture signal is thereby employed to identify the correct set of N+1 coefficients that is retrieved from the memory 370 and is employed by the status processor 380 to calculate the hemodynamic status index.

In FIG. 4, the impedance processor 340, the parameter processor 350, the status processor 380 and the optional threshold comparator 382, the therapy selector 384 and the model selector 398 have been exemplified as being run by the controller 360.

These units can then be implemented as a computer program product stored in the memory 370 and loaded and run on a general purpose or specially adapted computer, processor or microprocessor, represented by the controller 360 in FIG. 4. The software includes computer program code elements or software code portions effectuating the operation of the units. The program may be stored in whole or part, on or in one or more suitable computer readable media or data storage means that can be provided in an IMD 300.

In an alternative embodiment, the units are implemented as hardware units either forming part of the controller 360 or provided elsewhere in the IMD 300.

The IMD can in alternative embodiments be equipped with or connectable to another sensor as discussed above to generate a sense signal. This sense signal can then be used instead of or in addition to the impedance signal to calculate sensor-derivable parameters that are input, optionally together with impedance-derivable parameters, to the hemodynamic status model to assess the current hemodynamic status of the subject.

Figure 9:
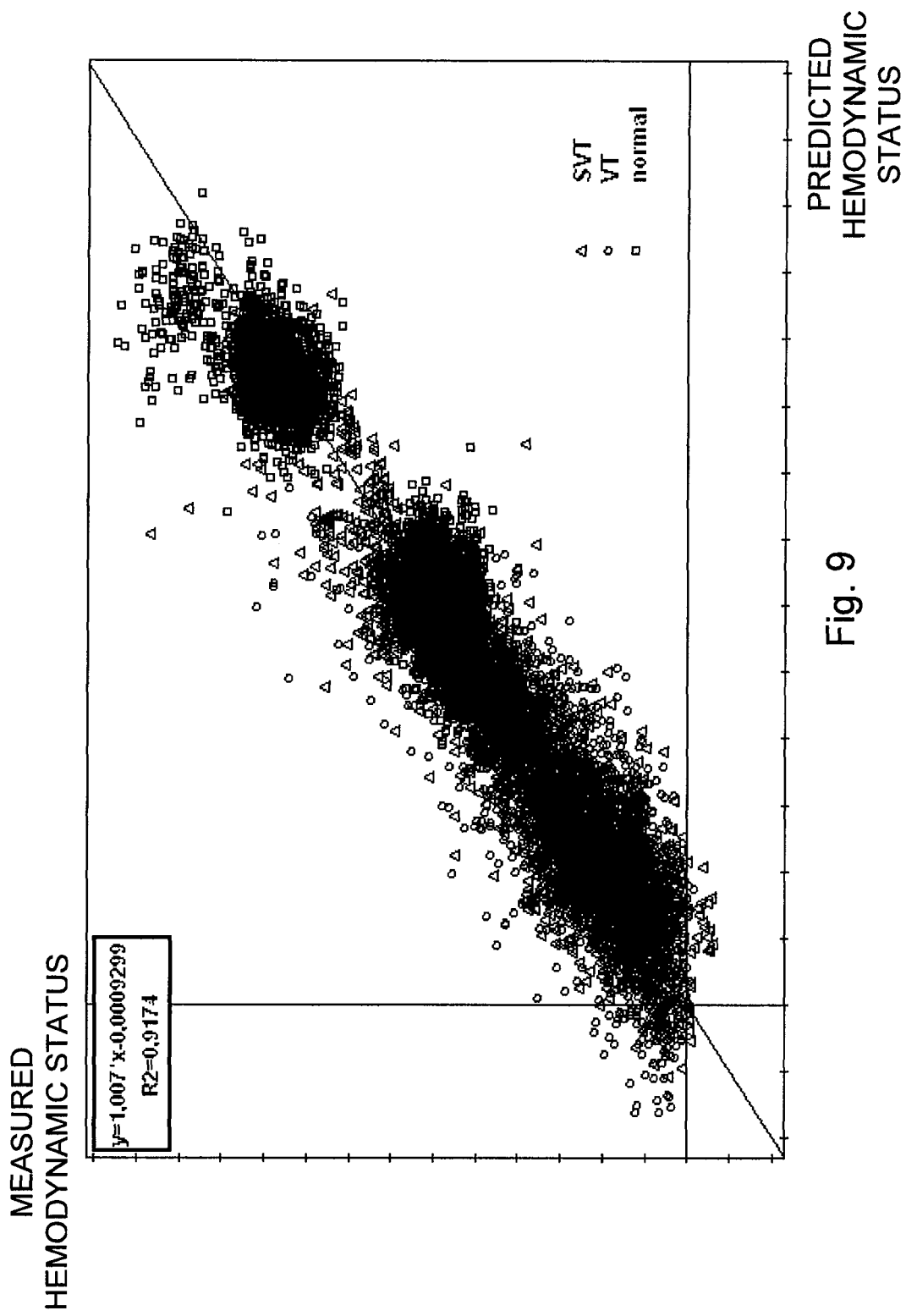
FIG. 9 is a diagram illustrating linear relationship between actual hemodynamic status and hemodynamic status predicted according to an embodiment for porcine subjects.

FIG. 9 is a diagram plotting measured hemodynamic status in terms of actual blood flow in porcine subjects and predicted hemodynamic status in terms of a hemodynamic status index according to an embodiment. Table 1 below lists the impedance-derivable parameters employed in the present experiment and the coefficients of the linear parametric status model calculated based on the impedance-derivable parameters. Data was collected during rapid stimulation mimicking arrhythmias in swine.

TABLE 1

Parameters and coefficients

| Impedance-derivable parameter | Coefficient |
|---|---|
| Average | 0.215500 |
| Linear fit - correlation coefficient | 0.201112 |
| Linear fit - gain | 0.198086 |
| Max index | 0.186976 |
| Fractionation | −0.181077 |
| Characteristic rate | −0.1666085 |
| Frequency integral parameter | −0.144627 |
| Average crossings | 0.121510 |
| Peak to peak | −0.120385 |
| Min index | 0.088288 |

Thus, the present embodiments can be efficiently employed to generate a patient-specific parametric status model that is employed to estimate the current hemodynamic status of the subject based on impedance measurements from the subject.

Figure 10:
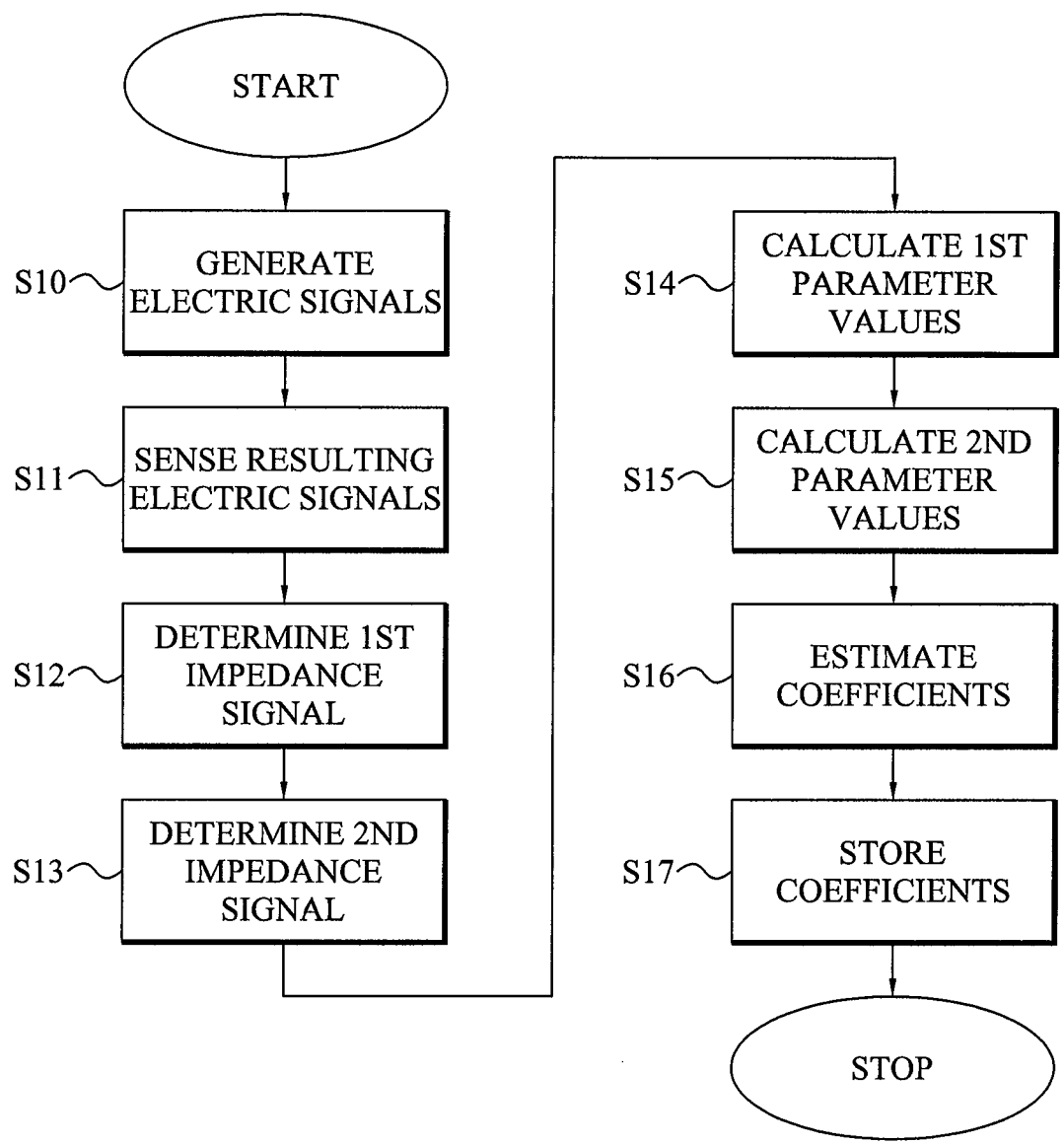
FIG. 10 is a flow diagram illustrating a method for determining a hemodynamic status model according to an embodiment.

FIG. 10 is a flow diagram illustrating an embodiment of determining a hemodynamic status model. The method starts in step S10 which generates electric signals that are applicable over two electrodes and over a portion of a subject's body during a period of normal hemodynamic status and in connection with a period of abnormal hemodynamic status. A next step S11 senses the resulting electric signals over two electrodes during the period of normal hemodynamic status and in connection with the period of abnormal hemodynamic status. A first impedance signal is determined in step S12 based on the electric signals applied and the resulting electric signals sensed during the period of normal hemodynamic status. A next step S13 correspondingly determines a second impedance signal based on the electric signals applied and the resulting electric signals sensed in connection with the period of abnormal hemodynamic status.

First parameter values of a set of N impedance-derivable parameters are calculated in step S14 based on the first impedance signals and corresponding second parameter values of the N impedance-derivable parameters are calculated based on the second impedance signal in step S15. The calculated first and second parameter values of steps S14 and S15 are employed in step S16 to estimate N+1 coefficients of a linear parametric status model as previously described. The estimated coefficients are stored in a memory in step S17 as representations of the linear parametric status.

The order of the method steps does not necessarily have to be as illustrated in FIG. 10. For instance, during the period of normal hemodynamic status electric signals are applied and resulting electric signals are sensed. The first impedance signal can then be determined and the first parameter values are calculated therefrom. These first parameter values can then be stored for later use in step S16 until sufficient numbers of first parameter values and second parameter values are available. Correspondingly, in connection with a period of abnormal hemodynamic status, electric signals are applied and resulting electric signals are sensed. The second impedance signal and the second parameter values are then determined therefrom. Only when sufficient numbers of such first and second parameter values are available the method continues to step S16. This means that in practice steps S10, S11, S12, S14 can be conducted several times during different periods of normal hemodynamic status and steps S10, S11, S13, S15 can correspondingly be conducted several times in connection with different periods of abnormal hemodynamic status.

As previously discussed, the period of abnormal hemodynamic status can be identified by detecting a tachyarrhythmia period of the subject based on electric signals sensed from the subject's heart. The generation of electric signals in step S10 and the sensing of resulting electric signals in step S11 with regard to periods of abnormal hemodynamic status can then be triggered based on such a detected tachyarrhythmia period.

The generation of electric signals in step S10 and the sensing of resulting electric signals in step S11 can be restricted to a predefined subject posture. The method then comprises detecting a current posture of the subject. Steps S10 and S11 are then performed during the period of normal hemodynamic status and in connection with the period of abnormal hemodynamic status when the subject is in a predefined target posture.

As previously described multiple linear parametric status models can be determined for the subject. In such a case, steps S10 and S11 are conducted in connection with multiple predefined postures of the subject as determined based on the detected current posture of the subject. Step S12 determines multiple impedance signals representative of normal hemodynamic status but for the different predefined postures and step S13 also determines multiple impedance signals representative of abnormal hemodynamic status for the different predefined postures. Steps S14 and S15 calculate a set of parameter values for each determined impedance signals and step S16 estimates the multiple linear parametric status models as discussed in the foregoing based on these sets of parameter values.

Figure 11:
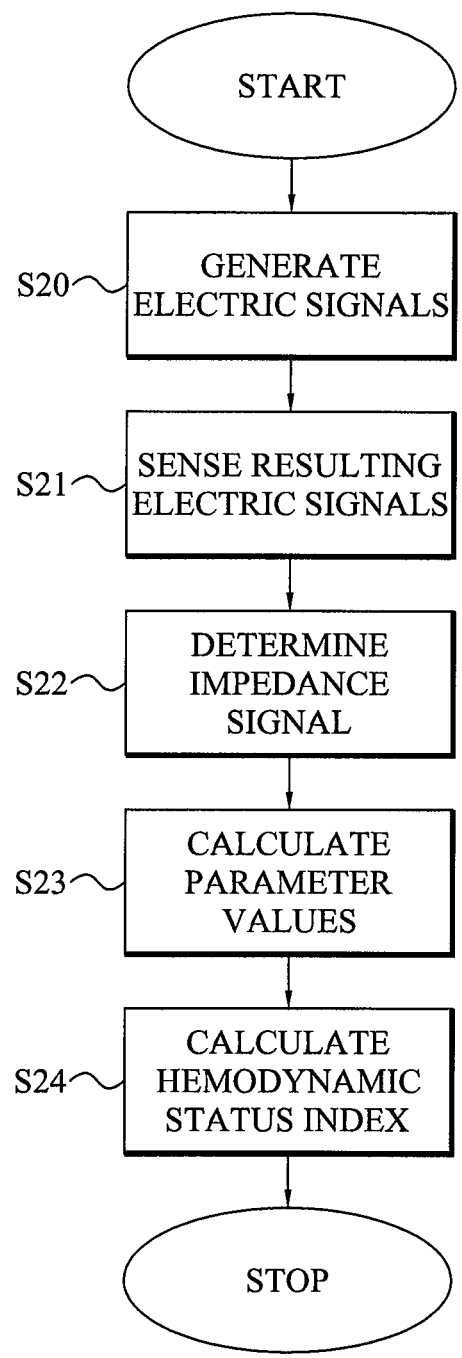
FIG. 11 is a flow diagram illustrating a method for assessing hemodynamic status according to an embodiment.

FIG. 11 is a flow diagram illustrating a method of assessing a hemodynamic status of a subject based on a linear parametric status model, such as determined according to FIG. 10. The method starts in step S20, which generates and applies electric signal to at least a portion of the subject during a status assessment period. Resulting electric signals are sensed in step S21 from the subject and are employed in step S22 to determine an impedance signal. Parameter values of the set of N different impedance-derivable parameters are calculated in step S23 based on the impedance signal determined in step S22. A hemodynamic status index representative of the current hemodynamic status of the subject is calculated in step S24 based on the calculated parameter values and the N+1 coefficients representative of the linear parametric status model.

The calculated hemodynamic status index can be compared with at least one threshold and this comparison is used to determine a suitable therapy, if any, to apply to the subject as previously described herein.

In similarity to the discussion in connection with FIG. 10, posture detection can also be used when applying the linear parametric status model to assess the hemodynamic status of the subject. For instance, the assessment can be limited to a predefined posture of the subject so that only impedance signals that are obtained when the subject is in the predefined posture will be employed in the assessment of hemodynamic status. Alternatively, the detected posture can be employed to select between multiple predefined linear parametric status models in order to identify the model that is adapted to the current posture of the subject during which the impedance measurements where conducted.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A system for determining a hemodynamic status model and providing therapy based on the hemodynamic status model, the system comprising:

a lead connector electrically connectable to at least two electrodes of at least one electric lead;

a signal generator connected to the lead connector and configured to generate, during a period of normal hemodynamic status of a subject and in connection with a period of abnormal hemodynamic status of the subject, electric signals applicable over two electrodes of the at least two electrodes;

a signal sensing unit connected to the lead connector and configured to sense, during the period of normal hemodynamic status of the subject and in connection with the period of abnormal hemodynamic status of the subject, resulting electric signals over two electrodes of the at least two electrodes;

an impedance processor configured to determine a first impedance signal based on the electric signals applied and the resulting electric signals sensed during the period of normal hemodynamic status of the subject and determine a second impedance signal based on the electric signals applied and the resulting electric signals sensed in connection with the period of abnormal hemodynamic status of the subject;

a parameter processor configured to calculate first parameter values of a set of N different impedance-derivable parameters based on the first impedance signal and calculate second parameter values of the set of N different impedance-derivable parameters based on the second impedance signal, N is a positive integer equal to or larger than two;

a model processor configured to estimate based on the first parameter values and the second parameter values, N+1 coefficients of a linear parametric status model $$Index^j = c_0 + \sum_{i=1}^{N} c_i f_i^j,$$

where j=1, $2C_0, C_i$ represent the N+1 coefficients, $f_i^1$ represent the first parameter values, $f_i^2$ represent the second parameter values, Index$^1$ has a predefined first value representative of normal hemodynamic status of the subject and Index$^2$ has a predefined second value representative of abnormal hemodynamic status of the subject;

a memory configured to store the N+1 coefficients as representations of the linear parametric status model;

a tachyarrhythmia detector configured to generate a tachyarrhythmia signal in response to a tachyarrhythmia period of the subject detected by the tachyarrhythmia detector based on electric signals sensed from a heart of the subject by at least one electric lead of the at least one electric lead, wherein the signal generator is configured to generate, in connection with the period of abnormal hemodynamic , status of the subject and in response to the tachyarrhythmia signal, the electric signals applicable over the two electrodes of the at least two electrodes;

the signal sensing unit is configured to sense, in connection with the period of abnormal hemodynamic status of the subject and in response to the tachyarrhythmia signal, the resulting electric signals over the two electrodes of the at least two electrodes; and a therapy selector to provide therapy based on the tachyarrhythmia detector.

2. The system according to claim 1, further comprising a posture sensor configured to generate a posture signal representative of a current posture of the subject, wherein the signal generator is configured to generate the electric signal when the posture signal indicates that the subject is in a predefined target posture.

3. A system for determining a hemodynamic status model and providing therapy based on the hemodynamic status model, the system comprising:

a lead connector electrically connectable to at least two electrodes of at least one electric lead;

a signal generator connected to the lead connector and configured to generate, during a period of normal hemodynamic status of a subject and in connection with a period of abnormal hemodynamic status of the subject, electric signals applicable over two electrodes of the at least two electrodes;

a signal sensing unit connected to the lead connector and configured to sense, during the period of normal hemodynamic status of the subject and in connection with the period of abnormal hemodynamic status of the subject, resulting electric signals over two electrodes of the at least two electrodes;

an impedance processor configured to determine a first impedance signals based on the electric signals applied and the resulting electric signals sensed during the period of normal hemodynamic status of the subject and determine a second impedance signal based on the electric signals applied and the resulting electric signals sensed in connection with the period of abnormal hemodynamic status of the subject;

a parameter processor configured to calculate first parameter values of a set of N different impedance-derivable parameters based on the first impedance signal and calculate second parameter values of the set of N different impedance-derivable parameters based on the second impedance signal, N is a positive integer equal to or larger than two;

a model processor configured to estimate, based on the first parameter values and the second parameter values, N+1 coefficients of a linear parametric status model $$Index^j = c_0 + \sum_{i=1}^{N} c_i f_i^j,$$

where j=1, $2C_0$, $C_i$ represent the N+1 coefficients, $f_i^1$ represent the first parameter values, $f_i^2$ represent the second parameter values, Index$^1$ has a predefined first value representative of normal hemodynamic status of the subject and Index$^2$ has a predefined second value representative of abnormal hemodynamic status of the subject;

a memory configured to store the N+1 coefficients as representations of the linear parametric status model;

a posture sensor configured to generate a posture signal representative of a current posture of the subject, wherein the signal generator is configured to generate, during the period of normal hemodynamic status of the subject and when the posture signal represents a first predefined posture of the subject, during the period of normal hemodynamic status of the subject and when the posture signal represents a second predefined posture of the subject, in connection with the period of abnormal hemodynamic status of the subject and when the posture signal represents the first predefined posture of the subject, and in connection with the period of abnormal hemodynamic status of the subject and when the posture signal represents the second predefined posture of the subject, the electric signals applicable over two electrodes of the at least two electrodes;

the signal sensing unit is configured to sense, during the period of normal hemodynamic status of the subject and when the posture signal represents the first predefined posture of the subject, during the period of normal hemodynamic status of the subject and when the posture signal represents the second predefined posture of the subject, in connection with the period of abnormal hemodynamic status of the subject and when the posture signal represents the first predefined posture of the subject, and in connection with the period of abnormal hemodynamic status of the subject and when the posture signal represents the second predefined posture of the subject, the resulting electric signals over two electrodes of the at least two electrodes;

the impedance process or is configured to determine the first impedance signal based on the electric signals applied and the resulting electric signals sensed during the period of normal hemodynamic status of the subject and when the posture signal represents the first predefined posture of the subject, determine the second impedance signal based on the electric signals applied and the resulting electric signals sensed in connection with the period of abnormal hemodynamic status of the subject and when the posture signal represents the first predefined posture of the subject, determine a third impedance signal based on the electric signals applied and the resulting electric signals sensed during the period of normal hemodynamic status of the subject, and when the posture signal represents the second predefined posture of the subject, and determine a fourth impedance signal based on the electric signals applied and the resulting electric signals sensed in connection with the period of abnormal hemodynamic status of the subject and when the posture signal represents the second predefined posture of the subject;

the parameter processor is configured to calculate the first parameter values of the set of N different impedance-derivable parameters based on the first impedance signal, calculate the second parameter values of the set of N different impedance-derivable parameters based on the second impedance signal, calculate third parameter values of the set of N different impedance-derivable parameters based on the third impedance signal and calculate fourth parameter values of the set of N different impedance-derivable parameters based on the fourth impedance signal;

the model processor is configured to estimate, based on the first parameter values and the second parameter values, N+1 coefficients of a first linear parametric status model $$Index_1^j = c_0 + \sum_{i=1}^{N} c_i f_i^j,$$

where j=1, 2, $c_0$, $c_i$ represent the N+1 coefficients, $f_i^1$ represent the first parameter values, $f_i^2$ represent the second parameter values, $Index_1^1$ has the predefined first value representative of normal hemodynamic status of the subject and $Index_1^2$ has the predefined second value representative of abnormal hemodynamic status of the subject and estimate, based on the third parameter values and the fourth parameter values, N+1 coefficients of a second linear parametric status model $$Index_2^j = d_0 + \sum_{i=1}^{N} d_i g_i^j,$$

where j=1, 2, $d_0$, $d_i$ represent the N+1 coefficients, $g_i^1$ represent the third parameter values, $g_i^2$ represent the fourth parameter values, $Index_2^1$ has the predefined first value representative of normal hemodynamic status of the subject and $Index_2^2$ has the predefined second value representative of abnormal hemodynamic status of the subject;

the memory is configured to store the 2(N+1) coefficients as representations of the first and second linear parametric status models; and a therapy selector to provide therapy based on the determined hemodynamic status of the subject.

4. An implantable medical device comprising:
a lead connector electrically connectable to at least two electrodes of the at least one electric lead;
a signal generator connected to the lead connector and configured to generate, during a status assessment period, electric signals applicable over two electrodes of the at least two electrodes;
a signal sensing unit connected to the lead connector and configured to sense, during the status assessment period, resulting electric signals over two electrodes of the at least two electrodes;
an impedance processor configured to determine an impedance signal based on the electric signals applied and the resulting electric signals sensed during the status assessment period;
a parameter processor configured to calculate parameter values of a set of N different impedance-derivable parameters based on the impedance signal;

a status processor configured to a calculate an index representative of a current hemodynamic status of a subject based on the parameter values calculated by the parameter processor and N+1 coefficients of a linear parametric status model $$Index = c_0 + \sum_{i=1}^{N} c_i f_i,$$

wherein $c_0$, $c_i$ represent the N+1 coeffieients and $f_i$ represent the parameter values calculated by the d parameter processor;

a posture sensor configured to generate a posture signal representative of a current posture of the subject; and a model selector configured to select between a first linear parametric status model $$Index_1 = c_0 + \sum_{i=1}^{N} c_i f_i$$

and a second linear parametric status model $$Index_2 = d_0 + \sum_{i=1}^{N} d_i f_i$$

based on the posture signal, wherein $c_0$, $c_i$ represent N+1 coefficients applicable when the subject is in a first posture and $d_0$, $d_i$ represent N+1 coefficients applicable when the subject is in a second posture; and a therapy selector to provide therapy based on the determined hemodynamic status of the subject.

5. A method of determining a hemodynamic status model, and providing therapy based on the hemodynamic status model, the method comprising:
generating, during a period of normal hemodynamic status of a subject and in connection with a period of abnormal hemodynamic status of the subject, electric signals applicable over two electrodes of at least one electric lead;
sensing, during the period of normal hemodynamic status of the subject and in connection with the period of abnormal hemodynamic status of the subject, resulting electric signals over two electrodes of the at least one electric lead;
determining a first impedance signal based on the electric signals applied and the resulting electric signals sensed during the period of normal hemodynamic status of the subject;
determining a second impedance signal based on the electric signals applied and the resulting electric signals sensed in connection with the period of abnormal hemodynamic status of the subject;
calculating first parameter values of a set of N different impedance-derivable parameters based on the first impedance signal;
calculating second parameter values of the set of N different impedance-derivable parameters based on the second impedance signal, N is a positive integer equal to or larger than two;

estimating, based on the first parameter values and the second parameter values, N+1 coefficients of a linear parametric status model $$Index^j = c_0 + \sum_{i=1}^{N} c_i f_i^j,$$

where j=1, 2 $c_0$, $c_i$ represent N+1 coefficients, $f_i^1$ represent the first parameter values, $f_i^2$ represent the second parameter values, Index$^1$ has a predefined first value representative of normal hemodynamic status of the subject; and Index$^2$ has a predefined second value representative of abnormal hemodynamic status of the subject;

storing said N+1 coefficients as representations of the linear parametric status model in a memory;

detecting a tachyarrhythmia period of the subject based on electric signals sensed from a heart of the subject by at least one electric lead of the at least one electric lead, wherein generating the electric signals in connection with the period of abnormal hemodynamic status comprises generating, in connection with the period of abnormal hemodynamic status of the subject and in response to the detected tachyarrhythmia period, the electric signals applicable over the two electrodes;

sensing the resulting electric signals in connection with the period of abnormal hemodynamic status comprises sensing, in connection with the period of abnormal hemodynamic status of the subject and in response to the detected tachyarrhythmia period, the resulting electric signals over the two electrodes; and providing therapy based on the determined hemodynamic status of the subject.

6. A method of determining a hemodynamic status model and providing therapy based on the hemodynamic status model, the method comprising:

generating, during a period of normal hemodynamic status of a subject and in connection with a period of abnormal hemodynamic status of the subject, electric signals applicable over two electrodes of at least one electric lead;

sensing, during the period of normal hemodynamic status of the subject and in connection wit the period of abnormal hemodynamic status of the subject, resulting electric signals over two electrodes of the at least one electric lead;

determining a first impedance signal based on the electric signals applied and the resulting electric signals sensed during the period of normal hemodynamic status of the subject;

determining a second impedance signal based on the electric signals applied and the resulting electric signals sensed in connection with the period of abnormal hemodynamic status of the subject;

calculating first parameter values of a set of N different impedance-derivable parameters based on the first impedance signal;

calculating second parameter values of the set of N different impedance-derivable parameters based on the second impedance signal, N is a positive integer equal to or larger than two;

estimation, based on the first parameter values and the second parameter values, N+1 coefficients of a linear parametric status model $$Index^j = c_0 + \sum_{i=1}^{N} c_i f_i^j,$$

where j=1, 2 $c_0$, $c_i$ represent said N+1 coefficients, $f_i^1$ respesent the first parameter values, $f_i^2$ represent the second parameter values, Index$^1$ has a predefined first value representative of normal hemodynamic status of the subject and Index$^2$ has a predefined second value representative of abnormal hemodynamic status of the subject;

storing said N+1 coefficients as representations of the linear parametric status model in a memory;

detecting a current posture of the subject, wherein generating the electric signals comprises generating, during the period of normal hemodynamic status of the subject and when the current posture is a first predefined posture of the subject, during the period of normal hemodynamic status of the subject and when the current posture is a second predefined posture of the subject, in connection with the period of abnormal hemodynamic status of the subject and when the current posture is the first predefined posture of the subject, and in connection with the period of abnormal hemodynamic status of the subject and when the current posture is the second predefined posture of the subject, the electric signals applicable over the two electrodes;

sensing the resulting electric signals comprises sensing, during the period of normal hemodynamic status of the subject and when the current posture is the first predefined posture of the subject, during the period of normal hemodynamic status of the subject and when the current posture is the second predefined posture of the subject, in connection with the period of abnormal hemodynamic status of the subject and when the current posture is the first predefined posture of the subject, and in connection with the period of abnormal hemodynamic status of the subject and when the current posture is the second predefined posture of the subject, the resulting electric signals over the two electrodes;

determining the first impedance signal comprises determining the first impedance signal based on the electric signals applied and the resulting electric signals sensed during the period of normal hemodynamic status of subject and when the current posture is the first predefined posture of the subject;

determining the second impedance signal comprises determining the second impedance signal based on the electric signals applied and the resulting electric signals sensed in connection with the period of abnormal hemodynamic status of the subject and when the current posture is the first predefined posture of the subject, the method further comprises:

determining a third impedance signal based on the electric signals applied and the resulting electric signals sensed during the period of normal hemodynamic status of the subject and when current posture is the second predefined posture of the subject;

determining a fourth impedance signal based on the electric signals applied and the resulting electric signals sensed in connection with the period of abnormal hemodynamic status of the subject and when the current posture is the second predefined posture of the subject;

calculating third parameter values of the set of N different impedance-derivable parameters based on the third impedance signal; and calculating fourth parameter values of the set of N different impedance-derivable parameters based on the fourth impedance signal, wherein estimating the N+1 coefficients comprises:

estimating, based on the first parameter values and the second parameter values, N+1 coefficients of a first linear parametric status model $$Index_1^j = c_0 + \sum_{i=1}^{N} c_i f_i^j,$$

where j=1, 2, $c_0$, $c_i$ represent the N+1 coefficients, $f_i^1$ represent the first parameter values, $f_i^2$ represent the second parameter values, $Index_1^1$ has the predefined first value representative of normal hemodynamic status of the subject and $Index_1^2$ has the predefined second value representative of abnormal hemodynamic status of the subject;

estimating, based on the third parameter values and the fourth parameter values, N+1 coefficients of a second linear parametric status model $$Index_2^j = d_0 + \sum_{i=1}^{N} d_i g_i^j,$$

where j=1, 2, $d_0$, $d_i$ represent the N+1 coefficients, $g_i^1$ represent the third parameter values, $g_i^2$ represent the fourth parameter values, $Index_2^1$ has the predefined first value representative of normal hemodynamic status of the subject and $Index_2^2$ has the predefined second value representative of abnormal hemodynamic status of the subject; and storing the N+1 coefficients comprises storing the 2(N+1) coefficients as representations of the first and second linear parametric status models; and providing therapy based on the determined hemodynamic status of the subject.

7. A method of assessing a hemodynamic status of a subject and providing therapy based on the hemodynamic status, the method comprising:

generating, during a status assessment period, electric signals applicable over two electrodes of at least one electric lead;

sensing, during the status assessment period, resulting electric signals over two electrodes of the at least one electric lead;

determining an impedance signal based on the electric signals applied and the resulting electric signals sensed during the status assessment period;

calculating parameter values of a set of N different impedance-derivable parameters based on the impedance signal;

calculating an index representative of a current hemodynamic status of the subject based on the parameter values and N+1 coefficients of a linear parametric status model $$Index = c_0 + \sum_{i=1}^{N} c_i f_i,$$

wherein $c_0$, $c_i$ represent the N+1 coefficients and $f_i$ represent the parameter values;

detecting a current posture of the subject;
selecting between a first linear parametric status model $$Index_1 = c_0 + \sum_{i=1}^{N} c_i f_i$$

and a second linear parametric status model $$Index_2 = d_0 + \sum_{i=1}^{N} d_i f_i$$

based on the current posture, wherein $c_0$, $c_i$ represent N+1 coefficients applicable when the subject is in a first posture and $d_0$, $d_i$ represent N+1 coefficients applicable when the subject is in a second posture; and providing therapy based on the determined hemodynamic status of the subject.

* * * * *